United States Patent
Muchero et al.

(10) Patent No.: US 11,441,152 B2
(45) Date of Patent: Sep. 13, 2022

(54) METHODS FOR IMPROVING CALLUS FORMATION AND REGENERATION IN PLANTS

(71) Applicant: UT-Battelle, LLC, Oak Ridge, TN (US)

(72) Inventors: Wellington Muchero, Oak Ridge, TN (US); Gerald Tuskan, Oak Ridge, TN (US); Jin-Gui Chen, Oak Ridge, TN (US); Lee E. Gunter, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 113 days.

(21) Appl. No.: 16/525,724

(22) Filed: Jul. 30, 2019

(65) Prior Publication Data

US 2020/0032282 A1    Jan. 30, 2020

Related U.S. Application Data

(60) Provisional application No. 62/711,651, filed on Jul. 30, 2018.

(51) Int. Cl.
*C12N 15/82* (2006.01)

(52) U.S. Cl.
CPC ..... *C12N 15/8218* (2013.01); *C12N 15/8213* (2013.01)

(58) Field of Classification Search
CPC .................. C12N 15/8218; C12N 15/8241
See application file for complete search history.

(56) References Cited

PUBLICATIONS

Tuskan et al (The Genome of Black Cottonwood, Populus trichocarpa (Torr. & Gray). Science 313: 1596-1605, 2006) (Year: 2006).*
Tuskan et al (Defining the genetic components of callus formation: A GWAS approach. PLOS ONE. 1-18, 2018) (Year: 2018).*
Muchero et al (Genome-Wide Association Mapping Studies (GWAS) for identifying mutations underlying tissue regeneration. NSF Advisory Committee 2016, p. 299-322, published Dec. 2016) (Year: 2016).*
Friedberg (Automated protein function prediction—the genomic challenge. Brief. Bioinformatics. 7:225-242, 2006) (Year: 2006).*
Butt, S. J. et al. "Micro Propagation in Advanced Vegetable Production: A Review" Advancements in Life Sciences, Feb. 25, 2015, vol. 2, No. 2, pp. 48-57.
Gaur, A. et al. "In vitro Plant Regeneration Studies and Their Potential Applications in *Populus* spp.: a Review", Israel Journal of Plant Sciences, 2015, vol. 63, No. 2, pp. 77-84.
Iwase, A. et al., "*Arabidopsis* WIND1 Induces Callus Formation in Rapeseed, Tomato, and Tobacco", Plant Signaling & Behavior, 2013, vol. 8, pp. e27432-1-e27432-5.
Tuskan, G. A. et al., "Defining the Genetic Components of Callus Formation: A GWAS Approach", PloS One, Aug. 17, 2018, vol. 13, No. 8, pp. e0202519, 1-18.
Evans, L. M. et al, "Population Genomics of Populus trichocarpa Identifies Signatures of Selection and Adaptive Trait Associations", Nature Genetics, 2014, vol. 46, pp. 1089-1096.
Geraldes, A. et al., "A 34K SNP Genotyping Array for Populus trichocarpa: Design, Application to the Study of Natural Populations and Transferability to other *Populus* species", Molecular Ecology Resources, Mar. 2013, vol. 13, No. 2, pp. 306-323.
Guo, J. et al., "Highly Efficient Isolation of Populus Mesophyll Protoplasts and Its Application in Transient Expression Assays" PLoS One, Sep. 13, 2012, vol. 7, No. 9, pp. e44908, 8 pages.
Anzola J M et al., "Putative *Arabidopsis* Transcriptional Adaptor Protein (PROPORZ1) is Required to Modulate Histone Acetylation in Response to Auxin", PNAS 107(22): 10308-10313 (Jun. 1, 2010).
Ikeuchi M. et al., "Plant Callus: Mechanisms of Induction and Repression", The Plant Cell 25:3159-3173 (Sep. 2013).
Mei Y. et al., "Tomato Leaf Curl Yunnan Virus-Encoded C4 Induces Cell Division Through Enhancing Stability of Cyclin D1.1 via Impairing NbSkn-Mediated Phosphorylation in Nicotiana Benthamiana", PLoS Pathogens 14(1):1-27 (Jan. 2, 2018).
Invitation to Pay Additional Fees dated Sep. 20, 2019 received in International Application No. PCT/US19/44048 from the International Searching Authority.

* cited by examiner

*Primary Examiner* — Bratislav Stankovic
*Assistant Examiner* — Wayne Zhong
(74) *Attorney, Agent, or Firm* — Scully, Scott, Murphy & Presser, P.C.

(57) ABSTRACT

This disclosure provides methods of improving callus formation in plants. This disclosure further provides genetically engineered plants with improved callus formation.

12 Claims, 8 Drawing Sheets
(8 of 8 Drawing Sheet(s) Filed in Color)
Specification includes a Sequence Listing.

SEQUENCE LISTING

```
<160> NUMBER OF SEQ ID NOS: 28

<210> SEQ ID NO 1
<211> LENGTH: 30
<212> TYPE: DNA
<213> ORGANISM: Artificial Sequence
<220> FEATURE:
<223> OTHER INFORMATION: oligonucleotide
```

<400> SEQUENCE: 1
atggtacctg agactttca acaaagggta                              30

<210> SEQ ID NO 2
<211> LENGTH: 30
<212> TYPE: DNA
<213> ORGANISM: Artificial Sequence
<220> FEATURE:
<223> OTHER INFORMATION: oligonucleotide

<400> SEQUENCE: 2
ataagcttga tctagtaaca tagatgacac                              30

<210> SEQ ID NO 3
<211> LENGTH: 24
<212> TYPE: DNA
<213> ORGANISM: Artificial Sequence
<220> FEATURE:
<223> OTHER INFORMATION: oligonucleotide

<400> SEQUENCE: 3
ggtgctagta cttgtggcca aaga                                   24

<210> SEQ ID NO 4
<211> LENGTH: 22
<212> TYPE: DNA
<213> ORGANISM: Artificial Sequence
<220> FEATURE:
<223> OTHER INFORMATION: oligonucleotide

<400> SEQUENCE: 4
ttcctaagca ccgctctgag tc                                     22

<210> SEQ ID NO 5
<211> LENGTH: 23
<212> TYPE: DNA
<213> ORGANISM: Artificial Sequence
<220> FEATURE:
<223> OTHER INFORMATION: oligonucleotide

<400> SEQUENCE: 5
atatttgaca caggcagtgg tct                                    23

<210> SEQ ID NO 6
<211> LENGTH: 23
<212> TYPE: DNA
<213> ORGANISM: Artificial Sequence
<220> FEATURE:
<223> OTHER INFORMATION: oligonucleotide

<400> SEQUENCE: 6
gttaagtagg tgcacttcgg aga                                    23

<210> SEQ ID NO 7
<211> LENGTH: 26
<212> TYPE: DNA
<213> ORGANISM: Artificial Sequence
<220> FEATURE:
<223> OTHER INFORMATION: oligonucleotide

<400> SEQUENCE: 7
agatctcaaa cccagcaatt tactgc                                 26

<210> SEQ ID NO 8

```
<211> LENGTH: 26
<212> TYPE: DNA
<213> ORGANISM: Artificial Sequence
<220> FEATURE:
<223> OTHER INFORMATION: oligonucleotide

<400> SEQUENCE: 8
acacatcaat tgcagcagta tagtcg                                          26

<210> SEQ ID NO 9
<211> LENGTH: 27
<212> TYPE: DNA
<213> ORGANISM: Artificial Sequence
<220> FEATURE:
<223> OTHER INFORMATION: oligonucleotide

<400> SEQUENCE: 9
cagcttgctt gtctgattga atcaaca                                         27

<210> SEQ ID NO 10
<211> LENGTH: 26
<212> TYPE: DNA
<213> ORGANISM: Artificial Sequence
<220> FEATURE:
<223> OTHER INFORMATION: oligonucleotide

<400> SEQUENCE: 10
ggtgatcaat gttttccaag ctggag                                          26

<210> SEQ ID NO 11
<211> LENGTH: 22
<212> TYPE: DNA
<213> ORGANISM: Artificial Sequence
<220> FEATURE:
<223> OTHER INFORMATION: oligonucleotide

<400> SEQUENCE: 11
gccttcgtgg tggttattaa gc                                              22

<210> SEQ ID NO 12
<211> LENGTH: 22
<212> TYPE: DNA
<213> ORGANISM: Artificial Sequence
<220> FEATURE:
<223> OTHER INFORMATION: oligonucleotide

<400> SEQUENCE: 12
tccaacaatg gccagtaaac ac                                              22

<210> SEQ ID NO 13
<211> LENGTH: 1116
<212> TYPE: DNA
<213> ORGANISM: Populus balsamifera subsp. trichocarpa

<400> SEQUENCE: 13
atggcgaatt atgcacaggg aaatggtgac ttccccgcga ttccgactca cggcggccaa      60
ttcattcaat acaatatttt cggtaatctt tttgaaatca cgtcgaaata tcgacctccg     120
atcactccga ttggtcgtgg tgcctacggc atcgtctgct ctgtgttgaa ttcggagacg     180
aacgagatgg tggcggtgaa aagatagcc aacgcgtttg ataatcaaat ggacgccaag     240
cgcacccttc gtgagattaa actgcttcgc catttggatc acgaaaacgt tattggtatc     300
agagatgtca ttcctccacc tctacgcaga gaatttactg atgtctacat tgccatggaa     360
ctcatggaca ctgatcttca ccaaattatt cgttccaacc aaggtttgtc agaggagcat     420
```

-continued

```
tgtcagtact tcttgtatca gattcttcga ggactgaaat atatacactc tgctaatatt      480
atccatagag atctcaaacc cagcaattta ctgctaaatg caaattgtga cttgaagata      540
tgcgattttg gtctagctcg gccaacttcg gagaatgagt ttatgacaga gtatgttgtc      600
accagatggt atcgtgcacc tgagttgttg ctcaactcct ccgactatac tgctgcaatt      660
gatgtgtggt ctgtaggttg catctttatg gagcttatga atagaaaacc tctgtttcca      720
ggcaaagatc atgtccatca gatgcgctta ttgacagagc ttcttggcaa acccactgaa      780
tctgatcttg gttttgtccg gaatgaggat gcgagaagat acatccagca actcgactcg      840
catccccgtc ggtcattagc tgagcttttc ccacttgttc accctctggc cattgatctt      900
atagataaaa tgttgacatt cgatcccact aaaagaatta ctgttgaaga agcattggct      960
catccatacc ttgcaagatt acatgacata gcagatgaac cagtctgctt agagcctttc     1020
tcctttgaat ttgagcaaca acccttggca aagagcaaa tgaaggatat gatctatgag     1080
gaggctttag cacttaatcc agaatatgca tgctag                              1116
```

<210> SEQ ID NO 14
<211> LENGTH: 1620
<212> TYPE: DNA
<213> ORGANISM: Populus balsamifera subsp. trichocarpa

<400> SEQUENCE: 14

```
atggaattga ataccaagaa tccaaaatcg ccactccgg taaaagaccg tcatgggttt       60
caatcaaaat tatctgagaa ttcgaatcca aaccttttcc atttaagccc ttgttcaaaa      120
cccacaaatt ctccttcaac aaaatcccaa aaatctgcct ccaagaaccc gactttgaat      180
cccaatccag ccattttttc acccagaaaa aagattaggg aaagaaggtt tgtagtggca      240
aaaaagaatt cgaagaagga ctttgaat tcaaatccaa caactgtgga ttgtaagtgc      300
aaagagagat atgggggcag tgtaaagaag tgtttgtgtt tggcctatga gacattaagg      360
gcttcacagg aggagttctt caagaacaag aatgacgttg aagagaaagg tgaaacagat      420
aaagaaaagg cctttgatta taaagttggg agagaagttt cagaggagga gatagaagac      480
catttaatgg atcaaaatct tgatattgag gatagggaag gatcagatgc tcaatattcc      540
tgcgaaattg agaaatcggg acaaatgggt agttctaaaa tcaagagaag gagaaataaa      600
ttacttgaag aagcaagaga cagtgcacct gacaatggga aggtgaagca tttggttgag      660
gccttcgaga agcttttac cctaccaaat ccgaaagaat cagataggac tgaagaggag      720
gagataaagg agaatagaaa gaaggcaatg caatgggctt tgcctggatt ccagcttcct      780
aaagtgttgc ctgatactga gttctcttct tcattttcat tgccaggatt tcagcatgct      840
gaggtatctg agacaaacgt ctcttcttct tcattctgtc catctggttt ctttttgact      900
tctgagaatc tcggtctgga tacaaggatt tctatttcct cttcatggga tggcagtcaa      960
ggcagtaatt ctagcaggtc atctaacgga ggcaggagaa gccgaagaaa tagtgccgag     1020
tcaggtgcaa caaccggggg gaggagattg aagaagaagc agattaaaat cacaagccaa     1080
aagccattta agcttaggac agaacaaagg ggaagactga aggaagagga attcacaaag     1140
aagatacaag aaataatgac ggaagaggag aagctgcgga ttcctatcgc acaaggcctt     1200
ccttggacaa cagatgaacc agagtgccta atcaaacctc cggtgaaaga aaacaccagg     1260
cccattgacc tgaagctccg tagtgatatt cgagctgtgg agcgtgctga ctttgaccat     1320
caggtatctg agaagatgag cttgattgag caatacaaga tggaaagaga gaggcaacaa     1380
```

```
aagttggcag aagaggaaga ggtacgccga ttgagaaagg agctcgttcc aaaagcgcag   1440
cctatgccct atttcgaccg gccattcatt cccagaaggt caatgaagca tccaacaatg   1500
gcgaacgaag caaagctccg cagacacaag aagatcaagt tctgtcaatc ctggaacgat   1560
gtcagcagct acagttatga tcaacagagc aacaagaag atagaatagg tggtggttag    1620

<210> SEQ ID NO 15
<211> LENGTH: 3213
<212> TYPE: DNA
<213> ORGANISM: Populus balsamifera subsp. trichocarpa

<400> SEQUENCE: 15
atgcgcctgg ctaggttgga tgagttgcgg caggcggcta aaactggggt ggagatgcgt     60
tatgagagag aaagggagag gcttggaaca aaagtggagt tacgggttca gcaggctgaa    120
gcaaacagaa tgctcatgct caaggcatac agacaaagaa gggccacgct taaggagaga    180
acatcccaat cattgtcacg aagaatggcc cgggaaagta agtacaagga gcgtgtacgt    240
gctgcaatta ccaaaaaacg tgcagccgct gaaaagaagc gtatgggatt gctggaagct    300
gaaaagagga gggcatgtgc tagggtgttg caagttcagc gagtagccag gtctgtctct    360
caccaacgtg agattgagag gaggagaatg agggacaagc tggaagatcg actgcaaagg    420
gcaaagagac aaagagcaga atatttgagg cagagaggac ggcagcatag ctctgttcga    480
gtgaactgga ataagatgca caagcaggct gatctccttt ctagaaaatt agcaaggtgc    540
tggaggcagt tcctgaggtc aaggaggact accatagacc tggcaaaaga ctatgatgcc    600
ctgaaaatca tgaaaactg tgtgaagtcg atgccatttg aacagcttgc ttgtctgatt    660
gaatcaacag gtactcttca gactgtgaag gctctacttg atcgtgtgga gagccgcttt    720
agagtctcca tggctgttgc tgctatggat catccctcca gcttggaaaa cattgatcac    780
cttcttaaaa gagttgccac ccctaagaaa aggaggacta ctcctaggtc ctctatgagg    840
agcagagagg caaaacgagt aggtaccacc agggagtctg ccagaagtgc tgctacgttg    900
tcaaggtatc cagtgagaat tgttctttgt gcctacatga ttttaggaca tccagatgct    960
gttttcagtg tcaagggca gcgtgagatt gctctggcca agtctgctga agatttcatt   1020
cgagagtttg agttgttgat aaggattata ctggatgggc ccatgcacag ttctgatgag   1080
gattctgagt ccatgtcacc aaaacgttgt acgttcaggt ctcaacttgc agcttttgat   1140
aaagaatggt gctcctactt gaattgcttt gtggtgtgga aggttaagga tgctcagtca   1200
ttggaggagg acttggtgag agctgcgtgc agcttgaac tctctatgat ccaaaaatgc   1260
aagctcaccc cagaagggag tactgatgct cttactcatg atatgaaagc cattcagaaa   1320
caggttacag aagatcaaaa actattaagg gaaaaggttc aacacctgag tggagatgct   1380
ggtattgagc gaatggaaat tgcactatct gaaacacgat ctaggtactt tcaagctaag   1440
gaaaatggaa gtccagtagg gtctccaatc atacactttc tatctcctag catgcccca   1500 tcttctcctt ctgctactgg ctcggctaat agaaataatg tgagtgatgg tattgagagg   1560
ccaagccgtg tagttcgctc cttattcaga gaagatacct cctcagcaaa agaacctgct   1620
tcctctgcaa ccagcagcag ccacttcgat ggccagtcag gttctgctgt tgggaaatca   1680
ataacagaga atgaattgat cataaatgaa tttctccatg agcaacgcca tggttttatg   1740
gataggttca atcttgctga caaagatgaa aacagcctca ggaaaaggt gagagagaca   1800 atggaggcag cttcctggga tagtgttctg gaatccatga acaggatga gcccaagtat   1860 gagtgggtag ttcagcttgt gggggaggtg agggatgaaa ttcaggagct ggctcctgag   1920
```

| | |
|---|---|
| agctggaaac aagagattgt tgaaagtatc gatccagatc ttcttgctca ggttctaagg | 1980 |
| tcaggtaacc tggacgttgg ttactgtggg aagattctag agttcgcatt agttactttg | 2040 |
| cagaaactct cctctccagc ccatgaggat gaaatgaagg ccctgcatca gaaaatgtta | 2100 |
| aaagagttgg ctcggacttg tcaaaccgaa gatgaatcga agtattcaca tattgccaca | 2160 |
| atgatcaaag gtctgcgctt tgtgctgcag cagatacagg ctcttaagca agagattagt | 2220 |
| aaagcacgca taagaatgat ggagcctttg ttaacaggtc ctgctgcatt ggattatctt | 2280 |
| agaaaagctt ttgccaacca ttatgggtct gattcggatg cctgtaactc tctaccactg | 2340 |
| acaatgcagt ggctttcatc tgtaaagagt agtgaagatc aagagtggga agaacacaag | 2400 |
| aattctctct ggctttgaa gagccatgac agttcatcac gggttttgt acctctcacc | 2460 |
| tcccttagaa ctggtggaag ctttctggtc aaaacaaatg aaagtgtaat tgcttcttct | 2520 |
| tctgttgctt ctgagacaga taaccaacaa ccagaaccgg aatgcactgg tgaaagagtt | 2580 |
| gatttgttgg tgaggctagg attgttgaag ttagtgagtg agtttctgg tctaacaaaa | 2640 |
| gaagctctgc ctgaaacttt tatgctaaac ctgttacggt tgagggctgt gcaggctcaa | 2700 |
| attcagaaaa tcattgtaat ttctaccagc attctggttt gccggcaaac gctcctgatg | 2760 |
| gagcaagcag taaccagcag tgcagacatg gaaagcattc tgttagagtg cagcaataaa | 2820 |
| ctgtcggaag tcctggaccg tgttgatgac gctggtattg aagaaatagt tgaagtagtt | 2880 |
| agtgggttgt tgcaaggcga tgacaaggta gttgatgagg agaagcttaa gccaagaaag | 2940 |
| atagtcatgg ctaggatgtt agcaaagagc ttgcaggctg gggatctgat ttttgaaaaa | 3000 |
| gtttcccgtg ctgtccattt ggctctaaga ggaattgtgc ttggggcag tggaccctgg | 3060 |
| ggaagaaaat tagtagaaat ggcactcagg cagattggag ctgtcatgct gactaaaaga | 3120 |
| gtggtggcag ctgctgaagt attagtggtg gcagccaccg tatccactgg cattcacagg | 3180 |
| ccatggtatg taaatctgac cgataacctg tga | 3213 |

<210> SEQ ID NO 16
<211> LENGTH: 1368
<212> TYPE: DNA
<213> ORGANISM: Populus balsamifera subsp. trichocarpa

<400> SEQUENCE: 16

| | |
|---|---|
| atgtataggc gggagaaaac aatgagagag gaaagataca agcacggcat caagaaccca | 60 |
| tctttctctt catcacttct tgatgaaatc tatcgttcta ttgatgatgg tgaaccaaaa | 120 |
| cgtgaagagt tgaagttcta cagagaaaca atgccaaaga acaaaacaa aattggcagg | 180 |
| aacattggag gagaagcagg gatgccaact cttcaacgtg cttgtttgat cgagaaatgg | 240 |
| atggagcaga aggtcaccca aaaggtcatc actcaacaga ggcggcaaaa ctcaacagaa | 300 |
| cttgagagaa aagcacagct tgatcatgat cttgaccaag atgtcctgtt ttttagctca | 360 |
| acctcaacct cttcggattc tagctctggt gggttctcat cttctgacac agaatctatg | 420 |
| tacggtgcaa gatcaagggc ctcttctttc aatccaccaa gacctaagcc agtcaggaca | 480 |
| agcctgtccg ctcggtcagg aaaaacagag aaaacagaga ggactctgtt ccatgaacag | 540 |
| agggaactgc gtatgtttga tgattatcac tacagctctg cttcagaaca gacaccaagg | 600 |
| cttgaagaca acataatcaa gtccaaatca agagccttaa agatttacag caatctaaag | 660 |
| aaggtgaaac agccaatttc accaggtggg aagctggcga atttcctcaa ttccctcttc | 720 |
| accacaggga actcaaagaa atcaaagaat tcatcttcca taggaaactt tgatgaagaa | 780 |

| | |
|---|---|
| aggaaactta actcaggaca agcatcgacc tgctcttctg cttcatcatt ttcaagatca | 840 |
| tgcttgagca agcattcgcc atcgaccagg gaaaaattac gcaatggggt taaaaggagt | 900 |
| gttagatttt accctgtgag tgtaattgtt gatgaagatt gcaggccagt cggccacaaa | 960 |
| tcattatatg aagaggaaga atcaagtctc atgtctgttt ctctgccaac agcatggaaa | 1020 |
| ataggaaat caccatcaag aaaaactgat gatgagctga agtatcaagt aatggagaag | 1080 |
| agtaggagag ttgaggaggt ggctagagag ttcttgaagg atcaccgtca aaatcagaag | 1140 |
| aaaaatgatg ttactatgat tgatgttcgc ggaaaatata atgatcgcta tcacgatgag | 1200 |
| gatgaggatg aggatgacga tgctgcaagc tattcgagtt cggatttatt cgagcttgat | 1260 |
| caccttgcag taattggaaa cgatcgtagg tattgtgaag aacttcccgt gtacgaaact | 1320 |
| actcatcttg atactaatcg tgccattgct aatggcttga tagtgtag | 1368 |

<210> SEQ ID NO 17
<211> LENGTH: 1503
<212> TYPE: DNA
<213> ORGANISM: Populus balsamifera subsp. trichocarpa

<400> SEQUENCE: 17

| | |
|---|---|
| atgagggtga ggatcttgtg ttgctgctgc tgtctcatgt tgctgctgca gttgctggcg | 60 |
| aggcataata attgtttaag agaagaatat ttgtctcgca ttggcgctcc catgtcttct | 120 |
| aaatcactac tttcttttgt gatttatggt tttcttcttc tttccccttg taactctttg | 180 |
| aaggacaatg ccgatgaagg aacgagagca tattttcata ctctcaaaat cagttctctc | 240 |
| ccatcaacag aagtctgcaa ggaatcttcc aaagctctca acgagggttc atcatcccta | 300 |
| aaattagtac acaggttcgg tccatgcaat ccacacagaa catcaactgc tccagcatca | 360 |
| tccttcaacg aaatcctccg tcgagacaaa cttcgagtgg actcaattat tcaggcccgg | 420 |
| cgttcaatga acttgaccag cagtgttgag cacatgaaga gtagtgtccc gttctatggt | 480 |
| ctatccaaaa tcactgcaag tgactatatt gtcaacgttg aatcggcac gcccaagaag | 540 |
| gaaatgccac ttatatttga cacaggcagt ggtctcattt ggactcaatg taagccgtgc | 600 |
| aaggcttgct atccaaaagt acctgtgttc gatccaacca agtcagcttc attcaaaggc | 660 |
| cttccatgtt cctcaaagct atgccaatca atcaggcaag gatgctcctc tccgaagtgc | 720 |
| acctacttaa ctgcatatgt agacaacagc agctccacag gaactttggc caccgaaaca | 780 |
| atatcctta gccatttaaa gtacgacttc aagaacattt tgattggatg cagcgatcaa | 840 |
| gtatctggtg aatcacttgg agaatctggt ataatgggac taaaccgctc acctatatct | 900 |
| ttagcatcac aaactgctaa tatatacgac aaactcttct cttattgtat accgtcaact | 960 |
| cctggctcaa ctggtcatct tactttcggc ggcaaagtgc cgaatgatgt cagattctcc | 1020 |
| ccagtatcta aaacagcacc atcttcggac tacgacatca aaatgactgg aattagtgtt | 1080 |
| ggaggccgta actattgat agatgcatcg gcttttaaga tttctagcac catcgactct | 1140 |
| ggtgcagtgc tcactcggct gcctccgaag gcatactcgg cactgaggtc agtgttccga | 1200 |
| gaaatgatga aggttatcc tttgttggac caagatgact ttctagacac atgctatgac | 1260 |
| ttcagtaatt atagcacggt tgcaatacct tcgattagtg tgttcttcga aggtggcgtg | 1320 |
| gagatggata tcgatgtttc ggggatcatg tggcaggttc agggagcaa ggtgtactgc | 1380 |
| ttggcatttg cggaattgga tgacgaagtt tcaatctttg ggaattttca gcaaaagact | 1440 |
| tacacagtag tctttgatgg tgcgaaggaa aggattgggt ttgcccccgg tggctgtgac | 1500 |
| taa | 1503 |

<210> SEQ ID NO 18
<211> LENGTH: 672
<212> TYPE: DNA
<213> ORGANISM: Populus balsamifera subsp. trichocarpa

<400> SEQUENCE: 18

| | | |
|---|---|---|
| atggactacg atttcagaaa cagaacaagc tcaccgtacg acacaccatc gacgatgcac | 60 |
| agatcatcga cgccgtcaac agcaccacaa cctagccatc cgatgtacgg accaccttct | 120 |
| ctctatccaa cagtgaatca acctggtcac accgtaatcc ctcacgcacc ccgccaccat | 180 |
| tctttcactc aacaagcccc ctcctctcct tcctcaggat tagggattcg ggttatgata | 240 |
| aaaccggaat accgcatcac tcctccacca caattgacac cacaaatagt ggagattccg | 300 |
| cggagtagtt ttcagtttga ttttgagctt gagagacaga ttttagcgga agcggagaag | 360 |
| gatagcccga attggagtag gctgcttggt ttagaaaatt cgcctcccaa acctcctcca | 420 |
| attcttggtt cctctctcat tgttggaaaa tatcctgtgg tgagaaagta catttcaatg | 480 |
| ggactcaatc gagatgctgt tcctcttgca gttgcaaact atggagataa tccgccaaag | 540 |
| gttcaggaat tgtcaacgg ctacacccctt ctacaagaaa tgggatttcc atcaaacaag | 600 |
| gtagctgaag ctttactcat gtatgacaac aacacggacg aggcattggc acatttcctt | 660 |
| aacagttcat aa | 672 |

<210> SEQ ID NO 19
<211> LENGTH: 339
<212> TYPE: DNA
<213> ORGANISM: Populus balsamifera subsp. trichocarpa

<400> SEQUENCE: 19

| | | |
|---|---|---|
| atgacaacct caaaattta cattttcctt ctactttctg cagtcctagc cgtccgtgtg | 60 |
| tccctatcat catcaacagc agttgatttt ctccccttgg agtcgtcgtc ggagtgccgg | 120 |
| ggatccattg ctgaatgctt gatggatgag gagtttggga tggacacaga gagcaacagg | 180 |
| cgcattctag caacgtcgag gtacgtaagc tatggtgcgc tgaggaggaa cactgtacca | 240 |
| tgttcgagac gcggcgcctc gtattataat tgtcgacctg gagctcaggc taatccttac | 300 |
| tctcgcgggt gtagtcgtat tacacgctgc aggaattaa | 339 |

<210> SEQ ID NO 20
<211> LENGTH: 1323
<212> TYPE: DNA
<213> ORGANISM: Populus balsamifera subsp. trichocarpa

<400> SEQUENCE: 20

| | | |
|---|---|---|
| atgctggaca ctaatggagg cgcctcccta ccatcaacag gaacagacgc agaaaaacgc | 60 |
| cgagtcagct acttctacga acccacaatc ggtgagtact actacggtca aggccactca | 120 |
| atgaaacccc acagaatccg aatggcccac aacttgataa tcaactacgc tctccaccgt | 180 |
| cggatggaaa tcaaccgtcc attcccagca ggtcctgaag acataggggtg ttccattct | 240 |
| gatgattacg tggaattctt gtcttcagtg tcaccacaat cagcgagtga tccggcacat | 300 |
| gggaggcagt tgaagaggtt taatattggt gaagattgtc cggttttta tgggttattt | 360 |
| gagttttgtc aggcctctgc tggtggctca attggctgtg ctgttaagct taatagaggg | 420 |
| gatgctgata ttgctttgaa ttgggctggt ggcttacatc atgcgaagag gagtgaggct | 480 |
| tctgggttt gttatgttaa tgatattgtt cttggcattc ttgagttgct caaagttcat | 540 |

```
aagcgtgtat tgtatgtaga tattgatgtc caccatggcg atggtgttga ggaagcattc      600
tatactactg acagggttat gactgtgtcc ttccataaat atggagattt ctttccaggg      660
acggggcaca tcaaggacat tggagttggg aaagggaaga actatgccct gaatattcct      720
ttaaaagatg ggatggatga cgaatgtttc cgtgctctgt ttcggccact catccaaaaa      780
gtgatggagg tttatcaacc tgatgcagtt gttctccaat gtggagcaga ttcattatct      840
ggtgataggt tggggtgttt caacctgtct gttaagggcc atgcagactg ccttagattt      900
attagatctt ttaatgttcc tctgatgatc ttgggtgggg gtgggtatac tatcaggaat      960
gttgcccgtt gctggtgcta tgagacagca gttgcagttg gggtggaacc agataacaaa     1020
ttgccttaca atgagtacta cgagtacttt ggccctgaat acacacttca tgctgaccca     1080
tccaatatgg agaacctaaa cacacccaaa gacatggaga gaataaggaa catactgcta     1140
gagcaacttt ctagactgcc taatgctccc agtgtacctt ttcagacaac accagctaca     1200
actgaagttc cggaagagga tgaagagaac atggatcaaa gaccaaagcg tcatgtatgg     1260
aatggtgttg attatgagtc tgatcatgat gaagatgaga accggaacc cggatttttc     1320 tga                                                                    1323
```

<210> SEQ ID NO 21
<211> LENGTH: 371
<212> TYPE: PRT
<213> ORGANISM: Populus balsamifera subsp. trichocarpa

<400> SEQUENCE: 21

```
Met Ala Asn Tyr Ala Gln Gly Asn Gly Asp Phe Pro Ala Ile Pro Thr
1               5                   10                  15

His Gly Gly Gln Phe Ile Gln Tyr Asn Ile Phe Gly Asn Leu Phe Glu
            20                  25                  30

Ile Thr Ser Lys Tyr Arg Pro Pro Ile Thr Pro Ile Gly Arg Gly Ala
        35                  40                  45

Tyr Gly Ile Val Cys Ser Val Leu Asn Ser Glu Thr Asn Glu Met Val
    50                  55                  60

Ala Val Lys Lys Ile Ala Asn Ala Phe Asp Asn Gln Met Asp Ala Lys
65                  70                  75                  80

Arg Thr Leu Arg Glu Ile Lys Leu Leu Arg His Leu Asp His Glu Asn
                85                  90                  95

Val Ile Gly Ile Arg Asp Val Ile Pro Pro Leu Arg Arg Glu Phe
            100                 105                 110

Thr Asp Val Tyr Ile Ala Met Glu Leu Met Asp Thr Asp Leu His Gln
        115                 120                 125

Ile Ile Arg Ser Asn Gln Gly Leu Ser Glu Glu His Cys Gln Tyr Phe
    130                 135                 140

Leu Tyr Gln Ile Leu Arg Gly Leu Lys Tyr Ile His Ser Ala Asn Ile
145                 150                 155                 160

Ile His Arg Asp Leu Lys Pro Ser Asn Leu Leu Asn Ala Asn Cys
                165                 170                 175

Asp Leu Lys Ile Cys Asp Phe Gly Leu Ala Arg Pro Thr Ser Glu Asn
            180                 185                 190

Glu Phe Met Thr Glu Tyr Val Val Thr Arg Trp Tyr Arg Ala Pro Glu
        195                 200                 205

Leu Leu Leu Asn Ser Ser Asp Tyr Thr Ala Ala Ile Asp Val Trp Ser
    210                 215                 220

Val Gly Cys Ile Phe Met Glu Leu Met Asn Arg Lys Pro Leu Phe Pro
```

```
                225                 230                 235                 240
Gly Lys Asp His Val His Gln Met Arg Leu Leu Thr Glu Leu Leu Gly
                    245                 250                 255
Lys Pro Thr Glu Ser Asp Leu Gly Phe Val Arg Asn Glu Asp Ala Arg
                260                 265                 270
Arg Tyr Ile Gln Gln Leu Asp Ser His Pro Arg Arg Ser Leu Ala Glu
                275                 280                 285
Leu Phe Pro Leu Val His Pro Leu Ala Ile Asp Leu Ile Asp Lys Met
            290                 295                 300
Leu Thr Phe Asp Pro Thr Lys Arg Ile Thr Val Glu Glu Ala Leu Ala
305                 310                 315                 320
His Pro Tyr Leu Ala Arg Leu His Asp Ile Ala Asp Glu Pro Val Cys
                325                 330                 335
Leu Glu Pro Phe Ser Phe Glu Phe Glu Gln Pro Leu Ala Glu Glu
            340                 345                 350
Gln Met Lys Asp Met Ile Tyr Glu Glu Ala Leu Ala Leu Asn Pro Glu
            355                 360                 365
Tyr Ala Cys
        370

<210> SEQ ID NO 22
<211> LENGTH: 539
<212> TYPE: PRT
<213> ORGANISM: Populus balsamifera subsp. trichocarpa

<400> SEQUENCE: 22

Met Glu Leu Asn Thr Lys Asn Pro Lys Ser Ala Thr Pro Val Lys Asp
1               5                   10                  15
Arg His Gly Phe Gln Ser Lys Leu Ser Glu Asn Ser Asn Pro Asn Leu
                20                  25                  30
Ser His Leu Ser Pro Cys Ser Lys Pro Thr Asn Ser Pro Ser Thr Lys
            35                  40                  45
Ser Gln Lys Ser Ala Ser Lys Asn Pro Thr Leu Asn Pro Asn Pro Ala
        50                  55                  60
Ile Phe Ser Pro Arg Lys Lys Ile Arg Glu Arg Phe Val Val Ala
65                  70                  75                  80
Lys Lys Asn Ser Lys Lys Glu Thr Leu Asn Ser Asn Pro Thr Thr Val
                85                  90                  95
Asp Cys Lys Cys Lys Glu Arg Tyr Gly Gly Ser Val Lys Lys Cys Leu
                100                 105                 110
Cys Leu Ala Tyr Glu Thr Leu Arg Ala Ser Gln Glu Glu Phe Phe Lys
            115                 120                 125
Asn Lys Asn Asp Val Glu Glu Lys Gly Glu Thr Asp Lys Glu Lys Ala
        130                 135                 140
Phe Asp Tyr Lys Val Gly Arg Glu Val Ser Glu Glu Ile Glu Asp
145                 150                 155                 160
His Leu Met Asp Gln Asn Leu Asp Ile Glu Asp Arg Glu Gly Ser Asp
                165                 170                 175
Ala Gln Tyr Ser Cys Glu Ile Glu Lys Ser Gly Gln Met Gly Ser Ser
                180                 185                 190
Lys Ile Lys Arg Arg Arg Asn Lys Leu Leu Glu Glu Ala Arg Asp Ser
            195                 200                 205
Ala Pro Asp Asn Gly Lys Val Lys His Leu Val Glu Ala Phe Glu Lys
        210                 215                 220
```

-continued

```
Leu Phe Thr Leu Pro Asn Pro Lys Glu Ser Asp Arg Thr Glu Glu Glu
225                 230                 235                 240

Glu Ile Lys Glu Asn Arg Lys Lys Ala Met Gln Trp Ala Leu Pro Gly
            245                 250                 255

Phe Gln Leu Pro Lys Val Leu Pro Asp Thr Glu Phe Ser Ser Ser Phe
            260                 265                 270

Ser Leu Pro Gly Phe Gln His Ala Glu Val Ser Glu Thr Asn Val Ser
        275                 280                 285

Ser Ser Ser Phe Cys Pro Ser Gly Phe Phe Leu Thr Ser Glu Asn Leu
290                 295                 300

Gly Leu Asp Thr Arg Ile Ser Ile Ser Ser Ser Trp Asp Gly Ser Gln
305                 310                 315                 320

Gly Ser Asn Ser Ser Arg Ser Ser Asn Gly Gly Arg Arg Ser Arg Arg
                325                 330                 335

Asn Ser Ala Glu Ser Gly Ala Thr Thr Gly Gly Arg Arg Leu Lys Lys
            340                 345                 350

Lys Gln Ile Lys Ile Thr Ser Gln Lys Pro Phe Lys Leu Arg Thr Glu
            355                 360                 365

Gln Arg Gly Arg Leu Lys Glu Glu Phe Thr Lys Lys Ile Gln Glu
370                 375                 380

Ile Met Thr Glu Glu Glu Lys Leu Arg Ile Pro Ile Ala Gln Gly Leu
385                 390                 395                 400

Pro Trp Thr Thr Asp Glu Pro Glu Cys Leu Ile Lys Pro Val Lys
                405                 410                 415

Glu Asn Thr Arg Pro Ile Asp Leu Lys Leu Arg Ser Asp Ile Arg Ala
            420                 425                 430

Val Glu Arg Ala Asp Phe Asp His Gln Val Ser Glu Lys Met Ser Leu
435                 440                 445

Ile Glu Gln Tyr Lys Met Glu Arg Glu Arg Gln Lys Leu Ala Glu
    450                 455                 460

Glu Glu Glu Val Arg Arg Leu Arg Lys Glu Leu Val Pro Lys Ala Gln
465                 470                 475                 480

Pro Met Pro Tyr Phe Asp Arg Pro Phe Ile Pro Arg Arg Ser Met Lys
                485                 490                 495

His Pro Thr Met Ala Asn Glu Ala Lys Leu Arg Arg His Lys Lys Ile
            500                 505                 510

Lys Phe Cys Gln Ser Trp Asn Asp Val Ser Ser Tyr Ser Tyr Asp Gln
            515                 520                 525

Gln Ser Asn Lys Glu Asp Arg Ile Gly Gly Gly
        530                 535

<210> SEQ ID NO 23
<211> LENGTH: 1070
<212> TYPE: PRT
<213> ORGANISM: Populus balsamifera subsp. trichocarpa

<400> SEQUENCE: 23

Met Arg Leu Ala Arg Leu Asp Glu Leu Arg Gln Ala Ala Lys Thr Gly
1               5                   10                  15

Val Glu Met Arg Tyr Glu Arg Glu Arg Glu Arg Leu Gly Thr Lys Val
            20                  25                  30

Glu Leu Arg Val Gln Gln Ala Glu Ala Asn Arg Met Leu Met Leu Lys
        35                  40                  45

Ala Tyr Arg Gln Arg Arg Ala Thr Leu Lys Glu Arg Thr Ser Gln Ser
    50                  55                  60
```

-continued

```
Leu Ser Arg Arg Met Ala Arg Glu Ser Lys Tyr Lys Glu Arg Val Arg
 65                  70                  75                  80

Ala Ala Ile Asn Gln Lys Arg Ala Ala Glu Lys Lys Arg Met Gly
                 85                  90                  95

Leu Leu Glu Ala Glu Lys Arg Arg Ala Cys Ala Arg Val Leu Gln Val
            100                 105                 110

Gln Arg Val Ala Arg Ser Val Ser His Gln Arg Glu Ile Glu Arg Arg
            115                 120                 125

Arg Met Arg Asp Lys Leu Glu Asp Arg Leu Gln Arg Ala Lys Arg Gln
        130                 135                 140

Arg Ala Glu Tyr Leu Arg Gln Arg Gly Arg Gln His Ser Ser Val Arg
145                 150                 155                 160

Val Asn Trp Asn Lys Met His Lys Gln Ala Asp Leu Leu Ser Arg Lys
                165                 170                 175

Leu Ala Arg Cys Trp Arg Gln Phe Leu Arg Ser Arg Arg Thr Thr Ile
            180                 185                 190

Asp Leu Ala Lys Asp Tyr Asp Ala Leu Lys Ile Asn Glu Asn Cys Val
        195                 200                 205

Lys Ser Met Pro Phe Glu Gln Leu Ala Cys Leu Ile Glu Ser Thr Gly
210                 215                 220

Thr Leu Gln Thr Val Lys Ala Leu Leu Asp Arg Val Glu Ser Arg Phe
225                 230                 235                 240

Arg Val Ser Met Ala Val Ala Ala Met Asp His Pro Ser Ser Leu Glu
                245                 250                 255

Asn Ile Asp His Leu Leu Lys Arg Val Ala Thr Pro Lys Lys Arg Arg
            260                 265                 270

Thr Thr Pro Arg Ser Ser Met Arg Ser Arg Glu Ala Lys Arg Val Gly
        275                 280                 285

Thr Thr Arg Glu Ser Ala Arg Ser Ala Ala Thr Leu Ser Arg Tyr Pro
        290                 295                 300

Val Arg Ile Val Leu Cys Ala Tyr Met Ile Leu Gly His Pro Asp Ala
305                 310                 315                 320

Val Phe Ser Gly Gln Gly Gln Arg Glu Ile Ala Leu Ala Lys Ser Ala
                325                 330                 335

Glu Asp Phe Ile Arg Glu Phe Glu Leu Leu Ile Arg Ile Ile Leu Asp
            340                 345                 350

Gly Pro Met His Ser Ser Asp Glu Asp Ser Glu Ser Met Ser Pro Lys
        355                 360                 365

Arg Cys Thr Phe Arg Ser Gln Leu Ala Ala Phe Asp Lys Glu Trp Cys
        370                 375                 380

Ser Tyr Leu Asn Cys Phe Val Val Trp Lys Val Lys Asp Ala Gln Ser
385                 390                 395                 400

Leu Glu Glu Asp Leu Val Arg Ala Ala Cys Gln Leu Glu Leu Ser Met
                405                 410                 415

Ile Gln Lys Cys Lys Leu Thr Pro Glu Gly Ser Thr Asp Ala Leu Thr
            420                 425                 430

His Asp Met Lys Ala Ile Gln Lys Gln Val Thr Glu Asp Gln Lys Leu
        435                 440                 445

Leu Arg Glu Lys Val Gln His Leu Ser Gly Asp Ala Gly Ile Glu Arg
        450                 455                 460

Met Glu Ile Ala Leu Ser Glu Thr Arg Ser Arg Tyr Phe Gln Ala Lys
465                 470                 475                 480
```

-continued

Glu Asn Gly Ser Pro Val Gly Ser Pro Ile His Phe Leu Ser Pro
                485                 490                 495

Ser Met Pro Pro Ser Ser Pro Ser Ala Thr Gly Ser Ala Asn Arg Asn
        500                 505                 510

Asn Val Ser Asp Gly Ile Glu Arg Pro Ser Arg Val Val Arg Ser Leu
            515                 520                 525

Phe Arg Glu Asp Thr Ser Ser Ala Lys Glu Pro Ala Ser Ser Ala Thr
530                 535                 540

Ser Ser Ser His Phe Asp Gly Gln Ser Gly Ser Ala Val Gly Lys Ser
545                 550                 555                 560

Ile Thr Glu Asn Glu Leu Ile Ile Asn Glu Phe Leu His Glu Gln Arg
                565                 570                 575

His Gly Phe Met Asp Arg Phe Asn Leu Ala Asp Lys Asp Glu Asn Ser
            580                 585                 590

Leu Lys Glu Lys Val Arg Glu Thr Met Glu Ala Ala Phe Trp Asp Ser
        595                 600                 605

Val Leu Glu Ser Met Lys Gln Asp Glu Pro Lys Tyr Glu Trp Val Val
    610                 615                 620

Gln Leu Val Gly Glu Val Arg Asp Glu Ile Gln Glu Leu Ala Pro Glu
625                 630                 635                 640

Ser Trp Lys Gln Glu Ile Val Glu Ser Ile Asp Pro Asp Leu Leu Ala
                645                 650                 655

Gln Val Leu Arg Ser Gly Asn Leu Asp Val Gly Tyr Cys Gly Lys Ile
            660                 665                 670

Leu Glu Phe Ala Leu Val Thr Leu Gln Lys Leu Ser Ser Pro Ala His
        675                 680                 685

Glu Asp Glu Met Lys Ala Leu His Gln Lys Met Leu Lys Glu Leu Ala
    690                 695                 700

Arg Thr Cys Gln Thr Glu Asp Glu Ser Lys Tyr Ser His Ile Ala Thr
705                 710                 715                 720

Met Ile Lys Gly Leu Arg Phe Val Leu Gln Gln Ile Gln Ala Leu Lys
                725                 730                 735

Gln Glu Ile Ser Lys Ala Arg Ile Arg Met Met Glu Pro Leu Leu Thr
            740                 745                 750

Gly Pro Ala Ala Leu Asp Tyr Leu Arg Lys Ala Phe Ala Asn His Tyr
        755                 760                 765

Gly Ser Asp Ser Asp Ala Cys Asn Ser Leu Pro Leu Thr Met Gln Trp
    770                 775                 780

Leu Ser Ser Val Lys Ser Ser Glu Asp Gln Glu Trp Glu Glu His Lys
785                 790                 795                 800

Asn Ser Leu Leu Ala Leu Lys Ser His Asp Ser Ser Ser Arg Val Phe
                805                 810                 815

Val Pro Leu Thr Ser Leu Arg Thr Gly Gly Ser Phe Leu Val Lys Thr
            820                 825                 830

Asn Glu Ser Val Ile Ala Ser Ser Val Ala Ser Glu Thr Asp Asn
        835                 840                 845

Gln Gln Pro Glu Pro Glu Cys Thr Gly Glu Arg Val Asp Leu Leu Val
    850                 855                 860

Arg Leu Gly Leu Leu Lys Leu Val Ser Gly Val Ser Gly Leu Thr Lys
865                 870                 875                 880

Glu Ala Leu Pro Glu Thr Phe Met Leu Asn Leu Leu Arg Leu Arg Ala
                885                 890                 895

Val Gln Ala Gln Ile Gln Lys Ile Ile Val Ile Ser Thr Ser Ile Leu

```
                        900                 905                 910
Val Cys Arg Gln Thr Leu Leu Met Glu Gln Ala Val Thr Ser Ser Ala
            915                 920                 925

Asp Met Glu Ser Ile Leu Leu Glu Cys Ser Asn Lys Leu Ser Glu Val
            930                 935                 940

Leu Asp Arg Val Asp Asp Ala Gly Ile Glu Ile Val Glu Val Val
945                 950                 955                 960

Ser Gly Leu Leu Gln Gly Asp Asp Lys Val Val Asp Glu Glu Lys Leu
                965                 970                 975

Lys Pro Arg Lys Ile Val Met Ala Arg Met Leu Ala Lys Ser Leu Gln
            980                 985                 990

Ala Gly Asp Leu Ile Phe Glu Lys  Val Ser Arg Ala Val  His Leu Ala
            995                 1000                1005

Leu Arg  Gly Ile Val Leu Gly  Gly Ser Gly Pro Trp  Gly Arg Lys
    1010                1015                1020

Leu Val  Glu Met Ala Leu Arg  Gln Ile Gly Ala Val  Met Leu Thr
    1025                1030                1035

Lys Arg  Val Val Ala Ala Ala  Glu Val Leu Val Val  Ala Ala Thr
    1040                1045                1050

Val Ser  Thr Gly Ile His Arg  Pro Trp Tyr Val Asn  Leu Thr Asp
    1055                1060                1065

Asn Leu
    1070

<210> SEQ ID NO 24
<211> LENGTH: 455
<212> TYPE: PRT
<213> ORGANISM: Populus balsamifera subsp. trichocarpa

<400> SEQUENCE: 24

Met Tyr Arg Arg Glu Lys Thr Met Arg Glu Glu Arg Tyr Lys His Gly
1               5                   10                  15

Ile Lys Asn Pro Ser Phe Ser Ser Ser Leu Leu Asp Glu Ile Tyr Arg
            20                  25                  30

Ser Ile Asp Asp Gly Glu Pro Lys Arg Glu Glu Leu Lys Phe Tyr Arg
        35                  40                  45

Glu Thr Met Pro Lys Lys Gln Asn Lys Ile Gly Arg Asn Ile Gly Gly
50                  55                  60

Glu Ala Gly Met Pro Thr Leu Gln Arg Ala Cys Leu Ile Glu Lys Trp
65                  70                  75                  80

Met Glu Gln Lys Val Thr Gln Lys Val Ile Thr Gln Arg Arg Gln
                85                  90                  95

Asn Ser Thr Glu Leu Glu Arg Lys Ala Gln Leu Asp His Asp Leu Asp
            100                 105                 110

Gln Asp Val Leu Phe Phe Ser Ser Thr Ser Thr Ser Ser Asp Ser Ser
        115                 120                 125

Ser Gly Gly Phe Ser Ser Ser Asp Thr Glu Ser Met Tyr Gly Ala Arg
    130                 135                 140

Ser Arg Ala Ser Ser Phe Asn Pro Pro Arg Pro Lys Pro Val Arg Thr
145                 150                 155                 160

Ser Leu Ser Ala Arg Ser Gly Lys Thr Glu Lys Thr Glu Arg Thr Leu
                165                 170                 175

Phe His Glu Gln Arg Glu Leu Arg Met Phe Asp Asp Tyr His Tyr Ser
            180                 185                 190
```

```
Ser Ala Ser Glu Gln Thr Pro Arg Leu Glu Asp Asn Ile Ile Lys Ser
            195                 200                 205

Lys Ser Arg Ala Leu Lys Ile Tyr Ser Asn Leu Lys Lys Val Lys Gln
        210                 215                 220

Pro Ile Ser Pro Gly Gly Lys Leu Ala Asn Phe Leu Asn Ser Leu Phe
225                 230                 235                 240

Thr Thr Gly Asn Ser Lys Lys Ser Lys Asn Ser Ser Ile Gly Asn
            245                 250                 255

Phe Asp Glu Glu Arg Lys Leu Asn Ser Gly Gln Ala Ser Thr Cys Ser
            260                 265                 270

Ser Ala Ser Ser Phe Ser Arg Ser Cys Leu Ser Lys His Ser Pro Ser
            275                 280                 285

Thr Arg Glu Lys Leu Arg Asn Gly Val Lys Arg Ser Val Arg Phe Tyr
            290                 295                 300

Pro Val Ser Val Ile Val Asp Glu Asp Cys Arg Pro Val Gly His Lys
305                 310                 315                 320

Ser Leu Tyr Glu Glu Glu Ser Ser Leu Met Ser Val Ser Leu Pro
            325                 330                 335

Thr Ala Trp Lys Ile Gly Lys Ser Pro Ser Arg Lys Thr Asp Asp Glu
            340                 345                 350

Leu Lys Tyr Gln Val Met Glu Lys Ser Arg Arg Val Glu Glu Val Ala
            355                 360                 365

Arg Glu Phe Leu Lys Asp His Arg Gln Asn Gln Lys Lys Asn Asp Val
            370                 375                 380

Thr Met Ile Asp Val Arg Gly Lys Tyr Asn Asp Arg Tyr His Asp Glu
385                 390                 395                 400

Asp Glu Asp Glu Asp Asp Ala Ala Ser Tyr Ser Ser Ser Asp Leu
            405                 410                 415

Phe Glu Leu Asp His Leu Ala Val Ile Gly Asn Asp Arg Arg Tyr Cys
            420                 425                 430

Glu Glu Leu Pro Val Tyr Glu Thr Thr His Leu Asp Thr Asn Arg Ala
            435                 440                 445

Ile Ala Asn Gly Leu Ile Val
            450                 455

<210> SEQ ID NO 25
<211> LENGTH: 500
<212> TYPE: PRT
<213> ORGANISM: Populus balsamifera subsp. trichocarpa

<400> SEQUENCE: 25

Met Arg Val Arg Ile Leu Cys Cys Cys Cys Cys Leu Met Leu Leu Leu
1               5                   10                  15

Gln Leu Leu Ala Arg His Asn Asn Cys Leu Arg Glu Glu Tyr Leu Ser
            20                  25                  30

Arg Ile Gly Ala Pro Met Ser Ser Lys Ser Leu Leu Ser Phe Val Ile
            35                  40                  45

Tyr Gly Phe Leu Leu Ser Pro Cys Asn Ser Leu Lys Asp Asn Ala
        50                  55                  60

Asp Glu Gly Thr Arg Ala Tyr Phe His Thr Leu Lys Ile Ser Ser Leu
65                  70                  75                  80

Pro Ser Thr Glu Val Cys Lys Glu Ser Ser Lys Ala Leu Asn Glu Gly
                85                  90                  95

Ser Ser Ser Leu Lys Leu Val His Arg Phe Gly Pro Cys Asn Pro His
            100                 105                 110
```

```
Arg Thr Ser Thr Ala Pro Ala Ser Ser Phe Asn Glu Ile Leu Arg Arg
            115                 120                 125

Asp Lys Leu Arg Val Asp Ser Ile Ile Gln Ala Arg Arg Ser Met Asn
130                 135                 140

Leu Thr Ser Ser Val Glu His Met Lys Ser Ser Val Pro Phe Tyr Gly
145                 150                 155                 160

Leu Ser Lys Ile Thr Ala Ser Asp Tyr Ile Val Asn Val Gly Ile Gly
                165                 170                 175

Thr Pro Lys Lys Glu Met Pro Leu Ile Phe Asp Thr Gly Ser Gly Leu
            180                 185                 190

Ile Trp Thr Gln Cys Lys Pro Cys Lys Ala Cys Tyr Pro Lys Val Pro
            195                 200                 205

Val Phe Asp Pro Thr Lys Ser Ala Ser Phe Lys Gly Leu Pro Cys Ser
            210                 215                 220

Ser Lys Leu Cys Gln Ser Ile Arg Gln Gly Cys Ser Ser Pro Lys Cys
225                 230                 235                 240

Thr Tyr Leu Thr Ala Tyr Val Asp Asn Ser Ser Ser Thr Gly Thr Leu
                245                 250                 255

Ala Thr Glu Thr Ile Ser Phe Ser His Leu Lys Tyr Asp Phe Lys Asn
            260                 265                 270

Ile Leu Ile Gly Cys Ser Asp Gln Val Ser Gly Glu Ser Leu Gly Glu
            275                 280                 285

Ser Gly Ile Met Gly Leu Asn Arg Ser Pro Ile Ser Leu Ala Ser Gln
            290                 295                 300

Thr Ala Asn Ile Tyr Asp Lys Leu Phe Ser Tyr Cys Ile Pro Ser Thr
305                 310                 315                 320

Pro Gly Ser Thr Gly His Leu Thr Phe Gly Gly Lys Val Pro Asn Asp
                325                 330                 335

Val Arg Phe Ser Pro Val Ser Lys Thr Ala Pro Ser Ser Asp Tyr Asp
            340                 345                 350

Ile Lys Met Thr Gly Ile Ser Val Gly Gly Arg Lys Leu Leu Ile Asp
            355                 360                 365

Ala Ser Ala Phe Lys Ile Ser Ser Thr Ile Asp Ser Gly Ala Val Leu
            370                 375                 380

Thr Arg Leu Pro Pro Lys Ala Tyr Ser Ala Leu Arg Ser Val Phe Arg
385                 390                 395                 400

Glu Met Met Lys Gly Tyr Pro Leu Leu Asp Gln Asp Phe Leu Asp
                405                 410                 415

Thr Cys Tyr Asp Phe Ser Asn Tyr Ser Thr Val Ala Ile Pro Ser Ile
                420                 425                 430

Ser Val Phe Phe Glu Gly Gly Val Glu Met Asp Ile Asp Val Ser Gly
            435                 440                 445

Ile Met Trp Gln Val Pro Gly Ser Lys Val Tyr Cys Leu Ala Phe Ala
            450                 455                 460

Glu Leu Asp Asp Glu Val Ser Ile Phe Gly Asn Phe Gln Gln Lys Thr
465                 470                 475                 480

Tyr Thr Val Val Phe Asp Gly Ala Lys Glu Arg Ile Gly Phe Ala Pro
                485                 490                 495

Gly Gly Cys Asp
            500
```

<210> SEQ ID NO 26
<211> LENGTH: 223

<212> TYPE: PRT
<213> ORGANISM: Populus balsamifera subsp. trichocarpa

<400> SEQUENCE: 26

```
Met Asp Tyr Asp Phe Arg Asn Arg Thr Ser Ser Pro Tyr Asp Thr Pro
1               5                   10                  15

Ser Thr Met His Arg Ser Ser Thr Pro Ser Thr Ala Pro Gln Pro Ser
            20                  25                  30

His Pro Met Tyr Gly Pro Pro Ser Leu Tyr Pro Thr Val Asn Gln Pro
        35                  40                  45

Gly His Thr Val Ile Pro His Ala Pro Arg His His Ser Phe Thr Gln
    50                  55                  60

Gln Ala Pro Ser Ser Pro Ser Ser Gly Leu Gly Ile Arg Val Met Ile
65                  70                  75                  80

Lys Pro Glu Tyr Arg Ile Thr Pro Pro Gln Leu Thr Pro Gln Ile
                85                  90                  95

Val Glu Ile Pro Arg Ser Ser Phe Gln Phe Asp Phe Glu Leu Glu Arg
                100                 105                 110

Gln Ile Leu Ala Glu Ala Glu Lys Asp Ser Pro Asn Trp Ser Arg Leu
            115                 120                 125

Leu Gly Leu Glu Asn Ser Pro Pro Lys Pro Pro Ile Leu Gly Ser
    130                 135                 140

Ser Leu Ile Val Gly Lys Tyr Pro Val Val Arg Lys Tyr Ile Ser Met
145                 150                 155                 160

Gly Leu Asn Arg Asp Ala Val Pro Leu Ala Val Ala Asn Tyr Gly Asp
                165                 170                 175

Asn Pro Pro Lys Val Gln Glu Phe Val Asn Gly Tyr Thr Leu Leu Gln
            180                 185                 190

Glu Met Gly Phe Pro Ser Asn Lys Val Ala Glu Ala Leu Leu Met Tyr
        195                 200                 205

Asp Asn Asn Thr Asp Glu Ala Leu Ala His Phe Leu Asn Ser Ser
    210                 215                 220
```

<210> SEQ ID NO 27
<211> LENGTH: 112
<212> TYPE: PRT
<213> ORGANISM: Populus balsamifera subsp. trichocarpa

<400> SEQUENCE: 27

```
Met Thr Thr Ser Lys Phe Tyr Ile Phe Leu Leu Leu Ser Ala Val Leu
1               5                   10                  15

Ala Val Arg Val Ser Leu Ser Ser Ser Thr Ala Val Asp Phe Leu Pro
            20                  25                  30

Leu Glu Ser Ser Ser Glu Cys Arg Gly Ser Ile Ala Glu Cys Leu Met
        35                  40                  45

Asp Glu Glu Phe Gly Met Asp Thr Glu Ser Asn Arg Arg Ile Leu Ala
    50                  55                  60

Thr Ser Arg Tyr Val Ser Tyr Gly Ala Leu Arg Arg Asn Thr Val Pro
65                  70                  75                  80

Cys Ser Arg Arg Gly Ala Ser Tyr Tyr Asn Cys Arg Pro Gly Ala Gln
                85                  90                  95

Ala Asn Pro Tyr Ser Arg Gly Cys Ser Arg Ile Thr Arg Cys Arg Asn
            100                 105                 110
```

<210> SEQ ID NO 28
<211> LENGTH: 440

<212> TYPE: PRT
<213> ORGANISM: Populus balsamifera subsp. trichocarpa

<400> SEQUENCE: 28

```
Met Leu Asp Thr Asn Gly Gly Ala Ser Leu Pro Ser Thr Gly Thr Asp
1               5                   10                  15

Ala Glu Lys Arg Arg Val Ser Tyr Phe Tyr Glu Pro Thr Ile Gly Glu
            20                  25                  30

Tyr Tyr Tyr Gly Gln Gly His Ser Met Lys Pro His Arg Ile Arg Met
        35                  40                  45

Ala His Asn Leu Ile Ile Asn Tyr Ala Leu His Arg Arg Met Glu Ile
    50                  55                  60

Asn Arg Pro Phe Pro Ala Gly Pro Glu Asp Ile Gly Trp Phe His Ser
65                  70                  75                  80

Asp Asp Tyr Val Glu Phe Leu Ser Val Ser Pro Gln Ser Ala Ser
                85                  90                  95

Asp Pro Ala His Gly Arg Gln Leu Lys Arg Phe Asn Ile Gly Glu Asp
            100                 105                 110

Cys Pro Val Phe Tyr Gly Leu Phe Glu Phe Cys Gln Ala Ser Ala Gly
        115                 120                 125

Gly Ser Ile Gly Cys Ala Val Lys Leu Asn Arg Gly Asp Ala Asp Ile
    130                 135                 140

Ala Leu Asn Trp Ala Gly Gly Leu His His Ala Lys Arg Ser Glu Ala
145                 150                 155                 160

Ser Gly Phe Cys Tyr Val Asn Asp Ile Val Leu Gly Ile Leu Glu Leu
                165                 170                 175

Leu Lys Val His Lys Arg Val Leu Tyr Val Asp Ile Asp Val His His
            180                 185                 190

Gly Asp Gly Val Glu Glu Ala Phe Tyr Thr Thr Asp Arg Val Met Thr
        195                 200                 205

Val Ser Phe His Lys Tyr Gly Asp Phe Phe Pro Gly Thr Gly His Ile
    210                 215                 220

Lys Asp Ile Gly Val Gly Lys Gly Lys Asn Tyr Ala Leu Asn Ile Pro
225                 230                 235                 240

Leu Lys Asp Gly Met Asp Asp Glu Cys Phe Arg Ala Leu Phe Arg Pro
                245                 250                 255

Leu Ile Gln Lys Val Met Glu Val Tyr Gln Pro Asp Ala Val Val Leu
            260                 265                 270

Gln Cys Gly Ala Asp Ser Leu Ser Gly Asp Arg Leu Gly Cys Phe Asn
        275                 280                 285

Leu Ser Val Lys Gly His Ala Asp Cys Leu Arg Phe Ile Arg Ser Phe
    290                 295                 300

Asn Val Pro Leu Met Ile Leu Gly Gly Gly Gly Tyr Thr Ile Arg Asn
305                 310                 315                 320

Val Ala Arg Cys Trp Cys Tyr Glu Thr Ala Val Ala Val Gly Val Glu
                325                 330                 335

Pro Asp Asn Lys Leu Pro Tyr Asn Glu Tyr Tyr Glu Tyr Phe Gly Pro
            340                 345                 350

Glu Tyr Thr Leu His Ala Asp Pro Ser Asn Met Glu Asn Leu Asn Thr
        355                 360                 365

Pro Lys Asp Met Glu Arg Ile Arg Asn Ile Leu Leu Glu Gln Leu Ser
    370                 375                 380

Arg Leu Pro Asn Ala Pro Ser Val Pro Phe Gln Thr Thr Pro Ala Thr
385                 390                 395                 400
```

-continued

```
Thr Glu Val Pro Glu Glu Asp Glu Glu Asn Met Asp Gln Arg Pro Lys
            405                 410                 415

Arg His Val Trp Asn Gly Val Asp Tyr Glu Ser Asp His Asp Glu Asp
            420                 425                 430

Glu Lys Pro Glu Pro Gly Phe Phe
            435                 440
```

METHODS FOR IMPROVING CALLUS FORMATION AND REGENERATION IN PLANTS

CROSS REFERENCE TO RELATED APPLICATION

This application claims the benefit of priority from U.S. Provisional Application No. 62/711,651, filed Jul. 30, 2018, the entire contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-00OR22725 awarded by the U.S. Department of Energy. The government has certain rights in this invention.

INCORPORATION BY REFERENCE OF SEQUENCE LISTING

The Sequence Listing in the ASCII text file, named as 37200_4190.1_SequenceListing.txt of 50 KB, created on Jul. 22, 2019, and submitted to the United States Patent and Trademark Office via EFS-Web, is incorporated herein by reference.

BACKGROUND

Callus arises in plants through the cellular reprogramming of parenchyma cells (Braun A C., *Annual Review of Plant Physiology.* 1954; 5: 133-62), leading to a disorganized amorphic mass of rapidly dividing cells. Callus induction is triggered by variations in endogenous plant hormone levels that occur in response to physical or chemical stimuli (Skoog F. *Am J Bot.* 1944; 30: 19-24; Ikeuchi M. et al., *Plant Cell.* 2013; 25: 3159-73). There are several regulatory cascades and pathways that lead to cellular reprogramming, including a cytokinin-based route, an auxin-based route and a wound-induced route (Ikeuchi M. et al., *Plant Cell.* 2013; 25: 3159-73). Wound-induced cellular reprogramming can occur due to bacterial, viral, and/or insect attack, as well as physical abrasion. In vivo callus formation has been generally observed across all higher plant genera. It was first reported in excised stem tissue of poplar, which was subsequently induced to form roots and shoots (Simon S V., *Jahrb Wiss Bot.* 1908; 45: 351-478). Callus induction is the basis of many in vitro plant regeneration protocols (Skoog F. et al., *Symp Soc Exp Biol.* 1957; 11: 118-30) that are prerequisites for genetic engineering and genome editing (Liu D. et al., *Curr Opin Plant Biol.* 2016; 30: 70-7). Moreover, plant callus formation shares similar anatomical and physiologic features with human tumor formation (Birnbaum K D. Et al., *Cell.* 2008; 132: 697-710), highlighting the value of understanding the underlying mechanisms callus formation across the tree of life. Fully defining the genetic components of callus induction and formation is therefore of broad general interest to plant and animal biologists.

Individual species, as well as genotypes within a species, vary in their ability to form callus. Despite significant progress in the field (Butt S J. et al., *Advancements in Life Sciences.* 2015; 2: 48-57; Gaur A. et al., *Isr J Plant Sci.* 2016; 63: 77-84), some commercially important plant species or genotypes within species often lack effective in vitro culture and callus induction protocols. This is particularly true for non-domesticated *Populus*, and without this capacity, creation of transgenic plants is difficult. Since callus induction and proliferation is under genetic control and regulation, identifying the genes and regulatory elements that control callus formation has the potential to facilitate the development of in vitro systems in recalcitrant plant species.

BRIEF SUMMARY OF THE DISCLOSURE

An aspect of the disclosure is directed to a genetically modified plant, plant cell or plant tissue, wherein the expression of a gene selected from the group consisting of Potri.003G018500 (SOK1), Potri.009G066100 (MAPK3), Potri.012G083800, Potri.006G222700, Potri.008G208200, Potri.015G023600, Potri.004G118700, and Potri.018G014800 (CNDbr), or a homolog thereof, is altered in the plant, plant cell or plant tissue.

Another aspect of the disclosure is directed to a method for increasing callus formation in a plant, plant cell or plant tissue comprising altering in a plant, plant cell or plant tissue the expression of a gene selected from the group consisting of Potri.003G018500 (SOK1), Potri.009G066100 (MAPK3), Potri.012G083800, Potri.006G222700, Potri.008G208200, Potri.015G023600, Potri.004G118700, and Potri.018G014800 (CNDbr), or a homolog thereof.

In some embodiments, the gene is selected from the group consisting of Potri.003G018500 (SOK1), Potri.009G066100 (MAPK3), Potri.012G083800, Potri.006G222700, Potri.008G208200, and Potri.015G023600, and wherein the alteration comprises inactivation of the selected gene in the plant, plant cell or plant tissue, resulting in increased callus formation in the plant, plant cell or plant tissue.

In some embodiments, the inactivation of the selected gene is achieved by introducing a nucleic acid inhibitor of the selected gene to the plant, plant cell or plant tissue. In some embodiments, the nucleic acid inhibitor is selected from the group consisting of an antisense RNA, a small interfering RNA, an RNAi, a microRNA, an artificial microRNA, and a ribozyme.

In some embodiments, the inactivation of the selected gene is achieved by genome editing, which is achieved by a method selected from the group consisting of CRISPR/Cas system, Cre/Lox system, TALEN system, ZFNs system and homologous recombination. In some embodiments, the CRISPR-mediated genome editing comprises introducing into the plant a first nucleic acid encoding a Cas9 nuclease, a second nucleic acid comprising a guide RNA (gRNA), wherein said gRNA is specific to the selected gene.

In some embodiments, the gene is selected from the group consisting of Potri.004G118700, and Potri.018G014800 (CNDbr), and wherein the alteration comprises expressing in the plant an exogenous nucleic acid comprising the selected gene, resulting in increased callus formation in the plant, plant cell or plant tissue.

In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea,* and *Zoysia.*

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

Definitions

Figures 1A, 1B, 1C, 1D, 1E, 1F:
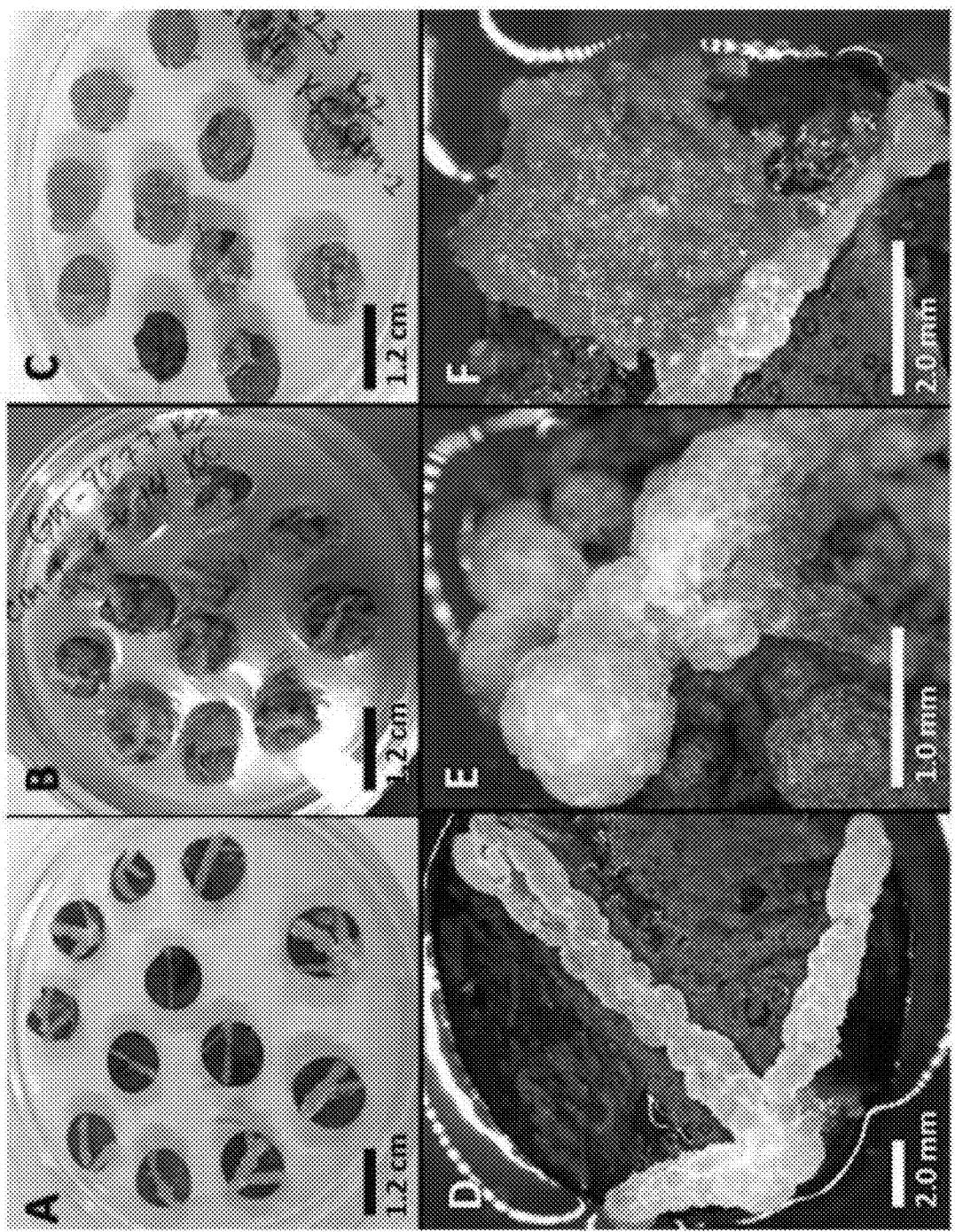
FIG. 1A-1F. Callus formation on *Populus* leaf disc explants after 30 days on a callus induction medium. (A) 12 replicate leaf disk explants with callus along the midrib, (B) 12 replicate leaf disk explants with callus across the explant, (C) 12 replicate leaf disk explants with callus along the cut margin, (D) white friable callus along the midrib, (E) light green compact callus, and (F) green friable callus.

Unless defined otherwise, all technical and scientific terms used herein have the same meaning as commonly understood by one of ordinary skill in the art to which this invention belongs.

As used herein, the term "about" refers to an approximately +/−10% variation from a given value.

An "altered level of gene expression" refers to a measurable or observable change in the level of expression of a transcript of a gene, or the amount of its corresponding polypeptide, relative to a control plant or plant cell under the same conditions (e.g., as measured through a suitable assay such as quantitative RT-PCR, a Northern blot, a Western blot or through an observable change in phenotype, chemical profile or metabolic profile). An altered level of gene expression can include up-regulated or down-regulated expression of a transcript of a gene or polypeptide relative to a control plant or plant cell under the same conditions. Altered expression levels can occur under different environmental or developmental conditions or in different locations than those exhibited by a plant or plant cell in its native state.

The term "control plant" as used herein refers to a plant cell, an explant, seed, plant component, plant tissue, plant organ, or whole plant used to compare against transgenic or genetically modified plant for the purpose of identifying an enhanced phenotype or a desirable trait in the transgenic or genetically modified plant. A "control plant" may in some cases be a transgenic plant line that comprises an empty vector or marker gene, but does not contain the recombinant polynucleotide of interest that is present in the transgenic or genetically modified plant being evaluated. A control plant may be a plant of the same line or variety as the transgenic or genetically modified plant being tested, or it may be another line or variety, such as a plant known to have a specific phenotype, characteristic, or known genotype. A suitable control plant would include a genetically unaltered or non-transgenic plant of the parental line used to generate a transgenic plant herein.

As used herein, the term "CRISPR" refers to a RNA-guided endonuclease comprising a nuclease, such as Cas9, and a guide RNA that directs cleavage of the DNA by hybridizing to a recognition site in the genomic DNA.

The term "DNA," as used herein, refers to a nucleic acid molecule of one or more nucleotides in length, wherein the nucleotide(s) are nucleotides. By "nucleotide" it is meant a naturally-occurring nucleotide, as well as modified versions thereof. The term "DNA" includes double-stranded DNA, single-stranded DNA, isolated DNA such as cDNA, as well as modified DNA that differs from naturally-occurring DNA by the addition, deletion, substitution and/or alteration of one or more nucleotides as described herein.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase and into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG)). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states.

The phrase "genetically modified," as used herein, refers to an organism whose genetic material has been altered by means of genetic engineering. Genetically modified organisms include genome-edited organisms, transgenic organisms, as well as organisms that were introduced exogenous nucleic acids into their cells.

The term "homolog" means a gene related to a second gene by descent from a common ancestral DNA sequence, therefore, the corresponding polynucleotide/polypeptide has a certain degree of homology, i.e., sequence identity (at least 40%, at least 60%, at least 65%, particularly preferred at least 66%, 68%, 70%, 75%, 80%, 86%, 88%, 90%, 92%, 95%, 97% or 99% sequence identity). A "homolog" furthermore means that the function is equivalent to the function of the original gene. Homologs of a given gene and homologous positions in the gene can be determined by sequence alignment programs, e.g., including but not limited to, NCBI BLAST, ClustalW, DIAMOND, CS-BLAST, and MAFFT.

As used herein, the term "nucleic acid" has its general meaning in the art and refers to a coding or non coding nucleic acid sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and noncoding region of a genome (i.e., nuclear or mitochondrial).

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell* 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

The vectors provided herein also can include, for example origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

General Description

Genetically Modified Plants

One aspect of the disclosure is directed to a genetically modified plant, plant cell or plant tissue that has improved or increased callus formation and regeneration capabilities. Also included herein are plant cells and plant tissue, all derived from the genetically modified plant of the disclosure. In addition, seeds which can germinate into a genetically modified plant as described herein are also provided.

In some embodiments, the expression of a gene selected from the group consisting of Potri.003G018500 (SOK1), Potri.009G066100 (MAPK3), Potri.012G083800, Potri.006G222700, Potri.008G208200, Potri.015G023600, Potri.004G118700, and Potri.018G014800 (CNDbr), or a homolog thereof, is altered in the genetically modified plant, plant cell or plant tissue as compared to a control plant which was not genetically modified.

In some embodiments, the gene with the altered expression is selected from the group consisting of Potri.003G018500 (SOK1), Potri.009G066100 (MAPK3), Potri.012G083800, Potri.006G222700, Potri.008G208200, and Potri.015G023600, and the alteration comprises inactivation of the selected gene in the plant, plant cell or plant tissue, resulting in increased callus formation in the plant, plant cell or plant tissue. The term "inactivation," as used herein, includes knocking out (e.g., deleting the gene using genome editing), knocking down (reducing the protein expression of a gene at least by 70%, at least 80%, at least 90%, at least 95%, or at least 99%, e.g., by using nucleic acid inhibitor), or abolishing at least one function (e.g., DNA binding ability, enzymatic activity etc.) of a gene.

In some embodiments, the inactivation of the selected gene is achieved by introducing a nucleic acid inhibitor of the selected gene to the plant. A "nucleic acid inhibitor" is a nucleic acid that can reduce or prevent expression or activity of a target gene. For example, an inhibitor of expression of a gene can reduce or eliminate transcription and/or translation of the gene product, thus reducing the gene protein expression.

In some embodiments, the nucleic acid inhibitor is selected from the group consisting of an antisense RNA, a small interfering RNA, an RNAi, a microRNA, an artificial microRNA, and a ribozyme.

In some embodiments, the inactivation of the selected gene is achieved by available gene targeting technologies in the art. Examples of gene targeting technologies include the Cre/Lox system (described in Kuhn, R., & M. Tones, R., 2002. *Transgenesis Techniques: Principles and Protocols*, 175-204.), homologous recombination (described in Capecchi, Mario R. 1989. *Science*, 244: 1288-1292), TALENs (described in Sommer et al., 2015. *Chromosome Research*, 23: 43-55, and Cermak et al., 2011. *Nucleic Acids Research: gkr*218.), and CRISPR Cas system as described in Ran F A et al., 2013. *Nature Protocols*.

In one embodiment, gene modulation is achieved by a CRISPR/Cas system. CRISPR-Cas and similar gene targeting systems are well known in the art with reagents and protocols readily available (Mali, P. et al., 2013. Science, 339(6121), 823-826; Hsu, P. D. et al., 2014. Cell, 157.6: 1262-1278; Jiang et al., 2013. Nature Biotechnology, 31, 233-239). Exemplary genome editing protocols are described in Jennifer Doudna, and Prashant Mali, 2016. "CRISPR-Cas: A Laboratory Manual" (CSHL Press, ISBN: 978-1-621821-30-4) and Ran, F. Ann, et al. 2013. Nature Protocols, 8 (11): 2281-2308.

A CRISPR endonuclease comprises two components: (1) an RNA-dependent nuclease, typically microbial Cas9; and (2) a short "guide RNA" (gRNA or sgRNA) comprising a 20-nucleotide targeting sequence that directs the nuclease to a location of interest in the genome. When co-expressed with an artificial sgRNA targeting a cellular gene, the Cas9 endonuclease generates double-stranded breaks of DNA at the targeted locus. In addition, when CRISPR endonuclease is supplemented with a stretch of DNA template homologous to the break region, the break is repaired using the supplied homologous DNA template via the process of homologous recombination (HR). CRISPR-mediated HR makes it possible to specifically edit the target DNA sequence and/or alter gene expression.

In some embodiments, the CRISPR-mediated genome editing comprises introducing into the plant a first nucleic acid encoding a Cas9 nuclease, a second nucleic acid comprising a guide RNA (gRNA), wherein said gRNA is specific to the selected gene.

In some embodiments, the gene with the altered expression is selected from the group consisting of Potri.004G118700, and Potri.018G014800 (CNDbr), and the alteration comprises expressing in the plant an exogenous nucleic acid comprising the selected gene, resulting in increased callus formation in the plant, plant cell or plant tissue.

Genetically modified plants of the disclosure are capable of self-pollinating or cross-pollinating with other plants of the same species so that the foreign gene, carried in the germ line, can be inserted into or bred into agriculturally useful plant varieties. The term "plant cell" as used herein, includes protoplasts, gamete producing cells, and cells which regenerate into whole plants. Accordingly, a seed comprising multiple plant cells capable of regenerating into a whole plant, is included in the definition of "plant cell."

In some embodiments, the genetically modified plant of the disclosure belongs to a recalcitrant plant species. The phrase "recalcitrant plant species" refers to plant species that are difficult to propagate in vitro under culture conditions. The phrase "recalcitrant plant species" also refers to plant species that do not readily produce calluses. The phrase "recalcitrant plant species" also refers to plant species that cannot be easily manipulated by genetic engineering methods.

In some embodiments, the genetically modified plant of the disclosure is a monocotyledonous plant. Examples of monocotyledonous plants include, but are not limited to, asparagus, field and sweet corn, barley, wheat, rice, sorghum, onion, pearl millet, rye and oats.

In some embodiments, the genetically modified plant of the disclosure is a dicotyledonous plant. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, *sequoia*, cedar, and oak.

In some embodiments, the plant is selected from the group consisting of genera Acer, Afzelia, *Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*.

Methods for Increasing Callus Formation and Regeneration in a Plant

This disclosure further provides methods for increasing callus formation and regeneration in a plant, plant cell or plant tissue.

In some embodiments, a method for increasing callus formation and/or regeneration in a plant, plant cell or plant tissue comprises altering in a plant, plant cell or plant tissue the expression of a gene selected from the group consisting of Potri.003G018500 (SOK1), Potri.009G066100 (MAPK3), Potri.012G083800, Potri.006G222700, Potri.008G208200, Potri.015G023600, Potri.004G118700, and Potri.018G014800 (CNDbr), or a homolog thereof.

In some embodiments, the gene is selected from the group consisting of Potri.003G018500 (SOK1), Potri.009G066100 (MAPK3), Potri.012G083800, Potri.006G222700, Potri.008G208200, and Potri.015G023600, and the alteration comprises inactivation of the selected gene in the plant, plant cell or plant tissue, resulting in increased callus formation in the plant, plant cell or plant tissue.

In some embodiments, the inactivation of the selected gene is achieved by introducing a nucleic acid inhibitor of the selected gene to the plant. In some embodiments, the nucleic acid inhibitor is selected from the group consisting of an antisense RNA, a small interfering RNA, an RNAi, a microRNA, an artificial microRNA, and a ribozyme.

In some embodiments, the inactivation of the selected gene is achieved by genome editing, which is achieved by a method selected from the group consisting of CRISPR/Cas system, Cre/Lox system, TALEN system, ZFNs system and homologous recombination.

In some embodiments, the gene is selected from the group consisting of Potri.004G118700, and Potri.018G014800 (CNDbr), and the alteration comprises expressing in the plant an exogenous nucleic acid comprising the selected gene, resulting in increased callus formation in the plant, plant cell or plant tissue.

In some embodiments, the plant belongs a to recalcitrant plant species.

In some embodiments, the plant is a monocotyledonous plant. Examples of monocotyledonous plants include, but are not limited to, asparagus, field and sweet corn, barley, wheat, rice, sorghum, onion, pearl millet, rye and oats.

In some embodiments, the plant is a dicotyledonous plant. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, and oak.

In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*.

Nucleic Acid Inhibitors

An aspect of the disclosure provides a number of nucleic acid based methods, including antisense RNA, ribozyme directed RNA cleavage, post-transcriptional gene silencing (PTGS), e.g., RNA interference (RNAi), microRNA and artificial microRNA and transcriptional gene silencing (TGS) that can be used to inhibit the expression of a gene selected from the group consisting of Potri.003G018500 (SOK1), Potri.009G066100 (MAPK3), Potri.012G083800, Potri.006G222700, Potri.008G208200, and Potri.015G023600, or a homolog thereof.

Suitable nucleic acid inhibitors, i.e., nucleic acids capable of inhibiting the expression of a target gene, include full-length nucleic acids of allelic variants of a gene selected from the group consisting of Potri.003G018500 (SOK1), Potri.009G066100 (MAPK3), Potri.012G083800, Potri.006G222700, Potri.008G208200, and Potri.015G023600, or a homolog thereof, or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant vector is then transformed into plants, as described below and the antisense strand of RNA is produced. The nucleic acid segment need not be the entire sequence of the gene to be repressed, but typically will be substantially complementary to at least a portion of the sense strand of the gene to be repressed.

In another method, a nucleic acid can be transcribed into a ribozyme or catalytic RNA, which affects expression of an mRNA. See, U.S. Pat. No. 6,423,885. Ribozymes can be designed to specifically pair with a target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes cleave mRNAs at locations dictated by flanking regions that form complementary base pairs with the target mRNA. See, for example, U.S. Pat. No. 5,254,678; Perriman et al., PNAS 92(13):6175-6179 (1995); de Feyter and Gaudron, Methods in Molecular Biology, Vol. 74, Chapter 43, Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof, of the polypeptide of interest. The length of the sequence that is similar or identical to the sense coding sequence can be from 10 nucleotides to 500 nucleotides, from 15 nucleotides to 300 nucleotides, from 20 nucleotides to 100 nucleotides or from 25 nucleotides to 100 nucleotides. The other strand of the stem portion of a double stranded RNA comprises a sequence that is similar or identical to the antisense strand or a fragment thereof, of the coding sequence of the polypeptide of interest and can have a length that is shorter, the same as or longer than the corresponding length of the sense sequence. In some cases, one strand of the stem portion of a double stranded RNA comprises a sequence that is similar or identical to the 3' or 5' untranslated region or a fragment thereof, of the mRNA encoding the polypeptide of interest and the other strand of the stem portion of the double stranded RNA comprises a sequence that is similar or identical to the sequence that is complementary to the 3' or 5' untranslated region, respectively or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest and the other strand of the stem portion comprises a sequence that is similar or identical to the sequence that is complementary to the sequence of the intron or fragment thereof in the pre-mRNA.

A construct including a sequence that is operably linked to a regulatory region and a transcription termination sequence and that is transcribed into an RNA that can form a double stranded RNA, can be transformed into plants as described below. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA or an intron in a pre-mRNA encoding a polypeptide of interest or a fragment of such sequences. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a P-DNA such that the left and right border-like sequences of the P-DNA are on either side of the nucleic acid.

In some embodiments, a suitable nucleic acid inhibitor can be a nucleic acid analog. Nucleic acid analogs can be modified at the base moiety, sugar moiety or phosphate backbone to improve, for example, stability, hybridization or solubility of the nucleic acid. Modifications at the base moiety include deoxyuridine for deoxythymidine and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite or an alkyl phosphotriester backbone.

Expression Vector Modulators

This disclosure provides an exogenous nucleic acid vector that comprises a nucleotide sequence that is transcribed into a nucleic acid inhibitor of a gene selected from the group consisting of Potri.003G018500 (SOK1), Potri.009G066100 (MAPK3), Potri.012G083800, Potri.006G222700, Potri.008G208200, and Potri.015G023600, operably linked to a regulatory region that is functional in a plant, plant cell or plant tissue as described above, where a plant, plant cell or plant tissue expressing such exogenous nucleic acid vector displays increased callus formation and regeneration properties compared to a control plant that does not comprise the nucleic acid vector.

In a specific embodiment, the Potri.003G018500 (SOK1) gene comprises a nucleotide sequence shown by SEQ ID NO: 15, encoding the protein SEQ ID NO: 23. In some embodiments, the Potri.003G018500 (SOK1) nucleotide sequence comprises a sequence that shows at least 90%, 91%, 92%, 93%, 94%, 95%, 96%, 97%, 98% or 99% identity to SEQ ID NO: 15. In some embodiments, the Potri.003G018500 (SOK1) the nucleotide sequence encodes a protein that shows at least 90%, 91%, 92%, 93%, 94%, 95%, 96%, 97%, 98% or 99% identity to SEQ ID NO: 23.

In a specific embodiment, the Potri.009G066100 (MAPK3) gene comprises a nucleotide sequence shown by SEQ ID NO: 13, encoding the protein SEQ ID NO: 21. In some embodiments, the Potri.009G066100 (MAPK3) nucleotide sequence comprises a sequence that shows at least 90%, 91%, 92%, 93%, 94%, 95%, 96%, 97%, 98% or 99% identity to SEQ ID NO: 13. In some embodiments, the Potri.009G066100 (MAPK3) nucleotide sequence encodes a protein that shows at least 90%, 91%, 92%, 93%, 94%, 95%, 96%, 97%, 98% or 99% identity to SEQ ID NO: 21.

In a specific embodiment, the Potri. 012G083800 gene comprises a nucleotide sequence shown by SEQ ID NO: 20, encoding the protein SEQ ID NO: 28. In some embodiments, the Potri. 012G083800 nucleotide sequence comprises a sequence that shows at least 90%, 91%, 92%, 93%, 94%, 95%, 96%, 97%, 98% or 99% identity to SEQ ID NO: 20. In some embodiments, the Potri. 012G083800 nucleotide sequence encodes a protein that shows at least 90%, 91%, 92%, 93%, 94%, 95%, 96%, 97%, 98% or 99% identity to SEQ ID NO: 28.

In a specific embodiment, the Potri. 006G222700 gene comprises a nucleotide sequence shown by SEQ ID NO: 16, encoding the protein SEQ ID NO: 24. In some embodiments, the Potri. 006G222700 nucleotide sequence comprises a sequence that shows at least 90%, 91%, 92%, 93%, 94%, 95%, 96%, 97%, 98% or 99% identity to SEQ ID NO: 16. In some embodiments, the Potri. 006G222700 nucleotide sequence encodes a protein that shows at least 90%, 91%, 92%, 93%, 94%, 95%, 96%, 97%, 98% or 99% identity to SEQ ID NO: 24.

In a specific embodiment, the Potri. 008G208200 gene comprises a nucleotide sequence shown by SEQ ID NO: 19, encoding the protein SEQ ID NO: 27. In some embodiments, the Potri. 008G208200 nucleotide sequence comprises a sequence that shows at least 90%, 91%, 92%, 93%, 94%, 95%, 96%, 97%, 98% or 99% identity to SEQ ID NO: 19. In some embodiments, the Potri. 008G208200 nucleotide sequence encodes a protein that shows at least 90%, 91%, 92%, 93%, 94%, 95%, 96%, 97%, 98% or 99% identity to SEQ ID NO: 27.

In a specific embodiment, the Potri. 015G023600 gene comprises a nucleotide sequence shown by SEQ ID NO: 18, encoding the protein SEQ ID NO: 26. In some embodiments, the Potri. 015G023600 nucleotide sequence comprises a sequence that shows at least 90%, 91%, 92%, 93%, 94%, 95%, 96%, 97%, 98% or 99% identity to SEQ ID NO: 18. In some embodiments, the Potri. 015G023600 nucleotide sequence encodes a protein that shows at least 90%, 91%, 92%, 93%, 94%, 95%, 96%, 97%, 98% or 99% identity to SEQ ID NO: 26.

This disclosure further provides an exogenous nucleic acid vector that comprises a nucleotide sequence that is transcribed into expression or overexpression of a gene selected from the group consisting of Potri.004G118700, and Potri.018G014800 (CNDbr), operably linked to a regulatory region that is functional in a plant as described above, where a plant, plant cell or plant tissue expressing such exogenous nucleic acid vector displays increased callus formation and regeneration properties compared to a control plant that does not comprise the nucleic acid vector.

In a specific embodiment, the nucleotide sequence comprises the Potri. 004G118700 gene shown by SEQ ID NO: 14, encoding the protein SEQ ID NO: 22. In some embodiments, the nucleotide sequence comprises a sequence that shows at least 90%, 91%, 92%, 93%, 94%, 95%, 96%, 97%, 98% or 99% identity to SEQ ID NO: 14. In some embodiments, the nucleotide sequence encodes a protein that shows at least 90%, 91%, 92%, 93%, 94%, 95%, 96%, 97%, 98% or 99% identity to SEQ ID NO: 22.

In a specific embodiment, the nucleotide sequence comprises the Potri. 018G014800 gene shown by SEQ ID NO: 17, encoding the protein SEQ ID NO: 25. In some embodiments, the nucleotide sequence comprises a sequence that shows at least 90%, 91%, 92%, 93%, 94%, 95%, 96%, 97%, 98% or 99% identity to SEQ ID NO: 17. In some embodiments, the nucleotide sequence encodes a protein that shows at least 90%, 91%, 92%, 93%, 94%, 95%, 96%, 97%, 98% or 99% identity to SEQ ID NO: 25.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

Some suitable regulatory regions initiate transcription, only or predominantly, in certain cell types. For example, a promoter that is active predominantly in a reproductive tissue (e.g., fruit, ovule or inflorescence) can be used. Thus, as used herein a cell type- or tissue-preferential promoter is one that drives expression preferentially in the target tissue, but may also lead to some expression in other cell types or tissues as well.

Root-active and root-preferential promoters confer transcription in root tissue, e.g., root endodermis, root epidermis or root vascular tissues. Root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990) and the tobacco RD2 promoter.

Promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab IR promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis* SUC2 sucrose-H+ symporter promoter (Truernit et al., *Planta*, 196:564-570 (1995)) and thylakoid membrane protein promoters from spinach (psaD, psaF, psaE, PC, FNR, atpC, atpD, cab, rbcS).

Lignin biosynthesis promoters are promoters that drive transcription of nucleic acids encoding enzymes involved in lignin biosynthesis. Examples of lignin biosynthesis promoters include promoters of the switchgrass (*Panicum virgatum*), rice (*Oryza sativa*), corn (*Zea mays*) and wheat (*Triticum aestivum*) homologs of the *Populus* cinnamate 4-hydroxylase, caffeoyl-CoA O-methyltransferase and caffeic acid O-methyltransferase genes. Also suitable are promoters of *Arabidopsis* genes encoding phenylalanin ammonia lyase (genomic locus At3g10340), trans-cinnamate 4-hydroxylase (genomic locus At2g30490), 4-coumarate:CoA ligase (genomic locus At1g51680), hydroxycinnamoyl-CoA:shikimate/quinate hydroxycinnamoyltransferase (genomic locus At5g48930), p-coumarate 3-hydroxylase (genomic locus At2g40890), caffeoyl-CoA 3-O-methyltransferase (genomic locus At4g34050), cinnamoyl CoA reductase (genomic locus At1g15950), ferulate 5-hydroxylase (genomic locus At4g36220), caffeic acid O-methyltransferase (genomic locus At5g54160) and cinnamyl alcohol dehydrogenase (genomic locus At4g34230).

Useful promoters also include cell wall related promoters, such as cellulose biosynthesis promoters. Cellulose biosynthesis promoters are promoters that drive transcription of nucleic acids encoding enzymes involved in cellulose biosynthesis. Examples of cellulose biosynthesis promoters include the promoter of the rice cellulose synthase gene (genomic locus Os08g25710), the promoter of the rice cellulose synthase gene (genomic locus Os08g06380) and the promoter of the rice cellulose synthase-like A2 gene (genomic locus Os10g26630).

Examples of promoters that have high or preferential activity in vascular bundles include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2):185-192 (1992)) and the rice tungro bacilliform virus (RTBV) promoter (Dai et al., *Proc. Natl. Acad. Sci. USA*, 101(2):687-692 (2004)). Promoters having preferential activity in the phloem region (e.g., primary phloem cells, companion cells and sieve cells), the xylem region (e.g., tracheids and vessels), the bundle sheath layer and/or the endodermis are also considered vascular tissue promoters. Promoters that have preferential activity in the pith, cortex, epidermis and/or in the vascular bundles or vascular layers of the stem are considered stem promoters. In some cases, the activity of stem promoters can also be induced by stress like drought.

Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators and inducible elements. Thus, for example, more than one regulatory region can be operably linked to the sequence of a polynucleotide encoding a Gene Y homolog or other lignin-modulating polypeptide. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

In one aspect, a plant cell comprising a Potri.003G018500 (SOK1), Potri.009G066100 (MAPK3), Potri.012G083800, Potri.006G222700, Potri.008G208200, or Potri.015G023600 nucleic acid inhibitor is provided. The plant cell comprises an exogenous nucleic acid, the exogenous nucleic acid comprising a regulatory region operably linked to a polynucleotide that is transcribed into an interfering RNA effective for inhibiting expression of Potri.003G018500 (SOK1), Potri.009G066100 (MAPK3), Potri.012G083800, Potri.006G222700, Potri.008G208200, or an allelic variant of any one of these genes. The exogenous nucleic acid can further comprise a 3' UTR operably linked to the polynucleotide. The polynucleotide can be transcribed into an interfering RNA comprising a stem-loop structure. The stem-loop structure can comprise an inverted repeat of the 3' UTR.

Methods of Use of Genetically Modified (Transgenic) Plants

This disclosure provides methods of using the disclosed plants with increased callus formation and regeneration properties in biofuel production processes. Methods of pretreatment and saccharification of biomass to fermentable sugars, followed by fermentation of the sugars to ethanol, are known in the art.

This disclosure further provides methods of using the disclosed genetically modified plants with increased callus formation and regeneration properties as starter plants for further plant propagation and/or genetic engineering.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

EXAMPLES

Example 1: Materials and Methods

Plant Materials

From within 1084 genotypes of Populus trichocarpa contained in the GWAS population (Geraldes A. et al, PLoS One, PMID: 23311503; Evans L M. et al, Nat Genet. 2014; 46: 1089-96) callus induction was tested in 280 genotypes. To avoid potential bias in allele frequencies, these genotypes were selected to represent the latitudinal gradient across the natural range of this species in the Pacific Northwest of North America. Global Position Systems (GPS) co-ordinates recorded when each genotype was originally collected were used to uniformly sample across river systems in this range (Slavov G T. et al., New Phytol. 2012; 196: 713-25). Clonal replicates of each genotype were grown in the greenhouse for three months prior to sampling leaf tissue for explant establishment. Each genotype had been re-sequenced to a minimum of an 18× depth and a SNP library with 8.2 million SNPs was available for the GWAS analyses. Whole-genome resequencing, alignment of Illumina short reads to the reference P. trichocarpa genome, SNP calling and data curation parameters are fully described by Evans et al. (Evans L M. et al, Nat Genet. 2014; 46: 1089-96).

Callus Induction

Multiple fully expanded leaves were collected from each genotype and surface disinfested using 1% (v/v) Tween-20 solution for 3 to 5 min, 70% (v/v) ethanol for 1 min, and 10% bleach solution (5.25% sodium hypochlorite) for 10 min, followed by 3 rinses with sterile, distilled water (Kang B-g. et al., Plant Cell, Tissue and Organ Culture (PCTOC). 2009; 99: 251). Explants were aseptically cut from leaves using a 1 $cm^2$ diameter cork borer and placed adaxial-side up on medium previously proven successful for callus induction of Populus trichocarpa (Meilan R, and Ma C., Agrobacterium Protocols Volume 2. Humana Press; 2007. pp. 143-51). Specifically, a Murashige and Skoog (MS) medium (Murashige T. et al. Physiol Plant. 1962; 15: 473-97) was supplemented with 0.5 µM 6-benzylaminopurine (BA), 0.5 µM zeatin, 5 µM naphthaleneacetic acid (NAA), 5 µM 2,4-D, and 1.28 mM 1-morpholinoethanesulfonic acid (MES), adjusted to a pH of 5.8, and solidified using 0.3% Phytoagar and 0.1% Gelrite. Midveins within the leaf explants were targeted as explants due to their organogenic potential. Three replications with 12 leaf disks per plate per replication were initiated. Cultures were then incubated for 4 weeks under constant dark at 25° C.

A second callus induction experiment was conducted using the seven genotypes each with the most and least prolific callus formation. Following the same protocol described above, leaf explants were cultured on media with varying phytohormone levels. Combinations of high and low cytokinin to auxin were tested: high cytokinin/low auxin with 5 µM BA+0.5 µM TDZ+0.5 µM NAA; high cytokinin/medium auxin with 5 µM BA+0.5 µM TDZ+1 µM NAA; high cytokinin/high auxin with 5 µM BA+0.5 µM TDZ+5 µM NAA; low cytokinin/low auxin with 1 µM BA+0.5 µM TDZ+0.5 µM NAA; low cytokinin/medium auxin with 1 µM BA+0.5 µM TDZ+1 µM NAA; low cytokinin/high auxin with 1 µM BA+0.5 µM TDZ+5 µM NAA. Three replications with 12 leaf disks per plate per replication were examined. Cultures were incubated for 4 weeks under constant dark at 25° C.

Callus Rating

The number of explants forming callus was counted and scored based on the amount of callus formed. Callus formation was recorded as a percent of the 12 explants per replicate forming callus. Callus ratings score were assigned as follows: 0 for no callus formation, 1 for compact callus, 2 for green friable callus, and 3 for white friable callus. Callus organogenic potential is known to vary by callus appearance (Meilan R, and Ma C., *Agrobacterium Protocols Volume* 2. Humana Press; 2007. pp. 143-51), with white friable callus leading to greater shoot induction potential. Location of callus formation on the explant was also noted as initiating from the midvein and/or from the cut edge.

Analysis of Variance

A two-way ANOVA, with genotype (G), replication (R) and G×R interaction as random effect sources of variation, was used to test for significant differences among genotypes in callus formation and callus rating (p≤0.05). Broad-sense heritability was calculated as the variance due to genotype divided by the summation of the error variance plus the genotype variance. Heritability was only calculated when there were significant genotype effects. A one-tailed t-test (p≤0.05) was used to test difference among hormone treatments in the second callus induction experiment.

Genome-Wide Association Test

To determine genetic loci associated with callus formation or callus rating, the EMMAX algorithm was used, with kinship as the correction factor for genetic background effects (Kang H M. et al, *Nat Genet.* 2010; 42: 348-54), to compute genotype-to-phenotype associations using 8.2 million SNPs with minor allele frequencies ≥0.05 as described by Zhang et al. (2018) (Zhang J. et al., *New Phytol.* 2018 July 11). Callus formation and callus rating candidate genes were identified based SNP association which exceeded the chromosome-wide-log 10 (p)=4.46 [p=3.47E-05] Bonferroni-adjusted significance threshold. GWAS tests were run independently by replicates and only those associations that were significant across all three replicates are reported here.

Gene Atlas Analysis

Gene Atlas data (Goodstein D M. et al., *Nucleic Acids Res.* 2011; 40(D1): D1178-D86) for four callus formation and four callus rating genes were collected from Phytomine database integrated in Phytozome (v.11.0) with FPKM value (Grigoriev I V. et al., *Nucleic Acids Res.* 2011; 40: D26-D32; Nordberg H. et al., *Nucleic Acids Res.* 2013; 42: D26-D31). The $\log_2$ scaled FPKM from a total of 24 different tissue types or conditions were subjected to 'gplots' of R package and summarized in heat maps (Warnes G R. et al., *R package version.* 2009; 2: 1).

Gene Co-Expression Network Construction and Gene Ontology Enrichment

Gene Atlas data across seven tissues was also used to calculate Pearson correlation coefficients between the expression profiles of all pairs of genes using the mcxarray and mcxdump programs from the MCL-Edge software package (Van Dongen S. *SIAM Journal on Matrix Analysis and Applications.* 2008; 30: 121-41). Correlation were calculated in a parallel fashion making use of the Parallel::MPI::Simple Perl module available on the Comprehensive Perl Archive Network (CPAN). A respective 0.8, and −0.8 Pearson threshold was applied and subnetworks of genes that co-express (positive or negative) with the eight candidate genes identified by GWAS were created and visualized in Cytoscape (Shannon P. et al., *Genome Res.* 2003; 13: 2498-504).

*Arabidopsis* Callus Orthologs

*Arabidopsis*-based microarray expression data was obtained from GSE29543, probes were mapped to the Affymetrix ATH1-121501 *Arabidopsis* annotation V35, expression was normalized using robust multi-array averaging (RMA) and then Linear Models for Microarray and RNA-Seq Data (Limma) was used to calculate differential expression. Time points of 12 h, 24 h, 48 h and 96 h of callus induction were compared to 0 h, representing establishment of shoot explants introduced to callus inducing media. A heat map was then constructed based on fold-change values from *Arabidopsis* genes that were significantly differentially expressed in shoot (adjusted p-value≤0.05) in at least one comparison and that were orthologs to *Populus* genes associated with callus formation.

Transient Overexpression in *Populus* Protoplast and Quantitative RT-PCR (qRT-PCR)

Protoplasts from hybrid poplar 717 (*Populus tremula* X *alba*) leaves were isolated and subsequently transfected as previously described (Guo J. et al., *PLoS One.* 2012; 7: e44908). The full-length CDS of LEC2 (Potri.004G045800) was determined according to the sequence information available at Phytozome. The CDS of LEC2 was introduced into the pENTR/D-TOPO vector (Life Technologies), and subsequently transferred into a Gateway destination vector via LR reaction. The Gateway destination vector was constructed by amplifying the 35S promoter, the Gateway cassette and the Tnos terminator from pGWB502 (Nakagawa T. et al., *Biosci, Biotechnol, Biochem.* 2007; 71: 2095-100), using primers 5'-ATGGTACCTGAGACTTTT-CAACAAAGGGTA-3' (SEQ ID NO: 1) and 5'-ATAAGCTTGATCTAGTAACATAGATGACAC-3' (SEQ ID NO: 2), was subcloned into the pUC19 vector using restriction enzymes KpnI and HindIII.

Total RNA from transfected and control *Populus* protoplasts was extracted using the Spectrum Plant Total RNA isolation kit (Sigma). One µg of total RNA were reversely transcribed to cDNA using RevertAid Reverse Transcriptase (Thermo Fisher Scientific). qRT-PCR was performed using Maxima SYBR Green/ROX qPCR Master Mix (Thermo Fisher Scientific). *Populus* Ubiquitin (UBQ10b) was used as an internal control for normalizing the relative transcript level. All PCR reactions were completed with at least three replicates. The primers used for qRT-PCR are listed in Table 1.

TABLE 1 qRT-PCR primers used in the transient protoplast assay.

| Gene Name | Gene ID | Primer | Primer Sequences |
|---|---|---|---|
| LEC2 | Potri.004G045800 | Forward | GGTGCTAGTACTTGTGGCCAAAGA (SEQ ID NO: 3) |
| | | Reverse | TTCCTAAGCACCGCTCTGAGTC (SEQ ID NO: 4) |

TABLE 1-continued qRT-PCR primers used in the transient protoplast assay.

| Gene Name | Gene ID | Primer | Primer Sequences |
|---|---|---|---|
| CNDbr | Potri.018G014800 | Forward | ATATTTGACACAGGCAGTGGTCT (SEQ ID NO: 5) |
|  |  | Reverse | GTTAAGTAGGTGCACTTCGGAGA (SEQ ID NO: 6) |
| MAPK3 | Potri.009G066100 | Forward | AGATCTCAAACCCAGCAATTTACTGC (SEQ ID NO: 7) |
|  |  | Reverse | ACACATCAATTGCAGCAGTATAGTCG (SEQ ID NO: 8) |
| SOK1 | Potri.003G018500 | Forward | CAGCTTGCTTGTCTGATTGAATCAACA (SEQ ID NO: 9) |
|  |  | Reverse | GGTGATCAATGTTTTCCAAGCTGGAG (SEQ ID NO: 10) |
| UBQ10b (Ctrl) | Potri.001G263000 | Forward | GCCTTCGTGGTGGTTATTAAGC (SEQ ID NO: 11) |
|  |  | Reverse | TCCAACAATGGCCAGTAAACAC (SEQ ID NO: 12) |

Example 2: Callus Formation and Rating is Genotype Dependent

Among the 280 *P. trichocarpa* genotypes tested for callus induction, 21 genotypes produced no callus and 30 genotypes formed callus from 100% of their explants (FIG. 1). The mean callus formation frequency across all genotypes was 53%+1.9% (mean+s.e.). Among those genotypes that did form callus; the mean callus rating was 1.3+0.05, with only 49 genotypes averaging a rating of 2.5 or higher. In total, 101 genotypes had a mean callus rating score of 1.0 or greater. Callus formation and callus rating were positively correlated with $r^2=0.77$. Of the explants that formed callus, 73% initiated from the midrib and 25% formed callus along the cut edge of the leaf explant. Genotype had a significant effect on callus formation (F279, 558=7.16, p-value=4.28E-86) and callus rating (F279, 558=6.56, p-value=5.42E-79). Broad-sense heritability for callus formation was $h2=0.67$ and heritability for callus rating $h2=0.65$.

Example 3: Candidate Genes Associated with Callus Formation and Rating

Among the 11 significant GWAS associations (Table 2), seven were significant for callus formation and four were selected for further study based on their repeated occurrence across biological replicates (FIG. 2A-2D)—Potri.003G018500 (SOK1), Potri.004G118700, Potri.009G066100 (MAPK3), and Potri.018G014800 (CNDbr) (p-value=9.90E-08, 4.27E-07, 9.72E-08 and 3.83E-07, respectively).

TABLE 2

Chromosome location for single nucleotide polymorphisms associations with *Populus* callus phenotypes that exceeded a Bonferroni-adjusted significance.

| Chr. | Position (bp) | -log p-value | Callus Phenotype |
|---|---|---|---|
| 3 | 2236428 | 9.90E−08 | Formation |
| 4 | 11078307 | 4.27E−07 | Formation |
| 6 | 22645602 | 9.89E−07 | Formation |
| 8 | 15806984 | 8.15E−07 | Formation |
| 9 | 6655602 | 9.72E−08 | Formation |
| 9 | 6655627 | 6.98E−07 | Formation |
| 18 | 1206685 | 3.83E−07 | Formation |
| 1 | 23447383 | 7.15E−07 | Rating |
| 6 | 23519186 | 1.61E−07 | Rating |
| 12 | 11117487 | 5.44E−07 | Rating |
| 15 | 1835111 | 6.53E−07 | Rating |

Chr. = Chromosome.

Potri.003G018500 (SOK1) encodes a SOK1 kinase containing a Testis-complex protein 11 motif that is highly expressed in early male flower development and co-expressed with Potri.015G078200—a gene of unknown function and Potri.016G082400—a kinesin motor protein-related protein ($r^2=0.89$ and $r^2=0.86$, respectively). Potri.004G118700, is a targeting protein for XKLP2 and is highly expressed in fully opened buds, immature leaves and root tips and is co-expressed with numerous genes including: Potri.002G080000—a mitotic-specific cyclin-B protein, Potri.016G033000—a cyclin G protein, Potri.017G081000—a tubulin, Potri.005G257500—a cyclin-dependent kinase and Potri.005G258300—a spindle checkpoint protein ($r2=0.99$, $r2=0.98$, $r2=0.98$ and $r2=0.96$, respectively). Potri.009G066100 (MAPK3) encodes a mitogen-activated protein kinase (MAPK3) which is highly expressed in roots under high nitrogen and urea and is co-expressed with many genes including Potri.008G082100—a cell cycle control protein and Potri.016G009700—a scarecrow-like protein ($r2=0.92$ and $r2=0.92$, respectively). Finally, Potri.018G014800 (CNDbr) is Chloroplast Nucleoid DNA-binding-related gene (CNDbr) which includes an aspartyl protease family protein domain, and is highly expressed in young leaves, stem nodes and internodes, root tips and in roots under high ammonia and nitrogen.

Among the 11 significant GWAS associations for callus rating, four were significant across all biological replicates (Table 2)—Potri.006G222700, Potri.008G208200, Potri.012G083800 and Potri.015G02360 (p-value=1.61E-07, 8.15E-07, 5.44E-07 and 6.53E-07, respectively) (FIG. 2E-2H). Potri.006G222700 is a gene of unknown function and is expressed in late development female flowers and dormant buds and is found in Salix purpurea, Theobroma cacao, and Manihot exculenta with >80% amino acid similarity. Potri.008G208200, a RALF-LIKE protein 22, is highly expressed in early developing male flowers. Potri.012G083800, a RPD3 histone deacetylase protein, is moderately expressed in dormant buds and is co-expressed with multiple genes including Potri.010G213700—a LEUKOCYTE RECEPTOR CLUSTER MEMBER 8 protein and Potri.009G137200—a transcriptional coactivator CAPER RRM superfamily protein ($r2=0.93$ and $r2=0.92$, respectively). Potri.015G023600, a second gene of unknown function, is moderately expressed in multiple tissues and is found in S. purpurea with >95% amino acid similarity. Interestingly, Potri.015G023600 contains a non-annotated RNA transcribed from the sequence between the 4th and 5th exons. This RNA is found in various tissues and contains no known domains or motifs. Potri.015G023600 is co-expressed with several zinc-finger proteins ($r^2=0.85-0.91$) and Potri.003G195400 encodes an ARMADILLO repeat-containing protein ($r^2=0.92$).

Figures 2A, 2B, 2C, 2D, 2E, 2F, 2G, 2H:
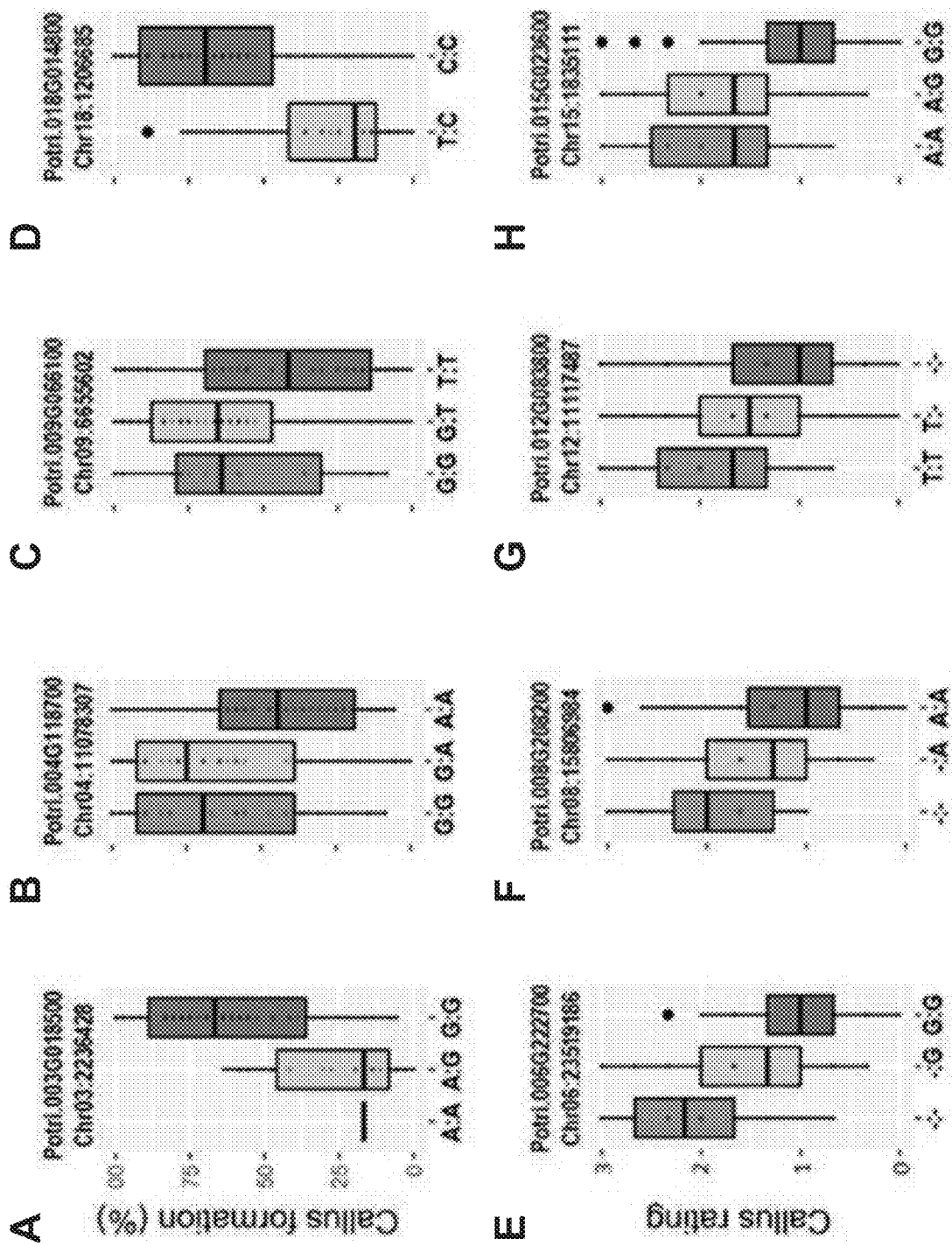
FIGS. 2A-2H. Box plots for (A-D) callus formation and (E-H) callus rating score from a genome-wide association test. (A) callus formation of Potri.003G018500 (SOK1), (B) callus formation of Potri.004G118700, (C) callus formation of Potri.009G066100, (D) callus formation of Potri.018G014800 (CNDbr), (E) callus rating score of Potri.006G222700, (F) callus rating score of Potri.008G208200, (G) callus rating score of Potri.012G083800, and (H) callus rating score of Potri.015G023600. In each panel, the homozygous rare (i.e., less common) alleles are displayed to the left in the red box, the heterozygous genotypes in the yellow box and the homozygous common alleles in the green box.

By examining the boxplots for each of the eight candidate genes, the inventors found that the rare allele (defined as the less frequent allele in the test population and depicted in the left column of each boxplot) for Potri.003G018500 (SOK1) and Potri.018G014800 (CNDbr) lead to reduced callus formation, whereas the rare allele for Potri.004G118700 and Potri.009G066100 (MAPK3) lead to increased callus formation (FIG. 2B and FIG. 2C). Interestingly, genotypes with homozygous rare alleles for Potri.003G018500 (SOK1) and Potri.018G014800 (CNDbr) were not found in the tested population, suggesting that this condition may be lethal. Callus rating scores were all higher for the rare alleles for Potri.006G222700, Potri.008G208200, Potri.012G083800, and Potri.015G023600 (FIG. 2E-2H). Three of the candidate genes identified via the GWAS analysis for callus rating were associated with small frameshift INDELs.

TABLE 3

Sequences for the Eight Candidate Genes

| Name | Nucleotide SEQ ID NO | Protein SEQ ID NO |
| --- | --- | --- |
| Potri.009G066100 | 13 | 21 |
| Potri.004G118700 | 14 | 22 |
| Potri.003G018500 | 15 | 23 |
| Potri.006G222700 | 16 | 24 |
| Potri.018G014800 | 17 | 25 |
| Potri.015G023600 | 18 | 26 |
| Potri.008G208200 | 19 | 27 |
| Potri.012G083800 | 20 | 28 |

Example 4: Callus Formation Validation

Callus formation in vitro, which is dependent on the plant source tissue and genetic background, varies with the concentration and ratios of added exogenous phytohormones to the plant media (Thorpe T A. Journal of Plant Biotechnology. 2000; 27: 245-58). The inventors therefore hypothesized that the Populus genotypes with the alleles associated with increased callus formation will consistently perform better in the different phytohormone treatments while those genotypes with the alleles associated with reduced callus formation will maintain reduced callus formation capacity due to their genetic background. To validate the initial callus formation experiment, and to leverage the information contained in the GWAS analyses, the inventors initiated an independent phytohormone treatment experiment based on six phytohormone combinations and seven genotypes that initially produced abundant callus with higher rating scores and contained the alleles associated with increased callus formation (i.e., BESC-18, BESC-233, BESC-823, GW-9795, GW-9877, GW-9920, and HOMB-21-2) and seven genotypes that had low occurrence of callus formation (i.e., BESC-100, BESC-106, BESC-352, BESC-856, BESC-89, GW-9904, and YALD-27-2). These genotypes were selected specifically because they contained high impact mutations (i.e., frameshifts or premature stop codons) predicted by genotype resequencing data using SnpEff in one or more of the significant loci identified in the GWAS results. Based on a one-tailed t-test, there were significant differences between the high callus producing genotypes and the low callus producing genotypes across all phytohormone combinations tested ($t=3.70$, $p=2.03E-3$). The abundant callus forming genotypes also had consistently higher callus rating scores across all phytohormone combinations, with the exception of genotypes BESC-18 and GW-9877.

Figure 3:
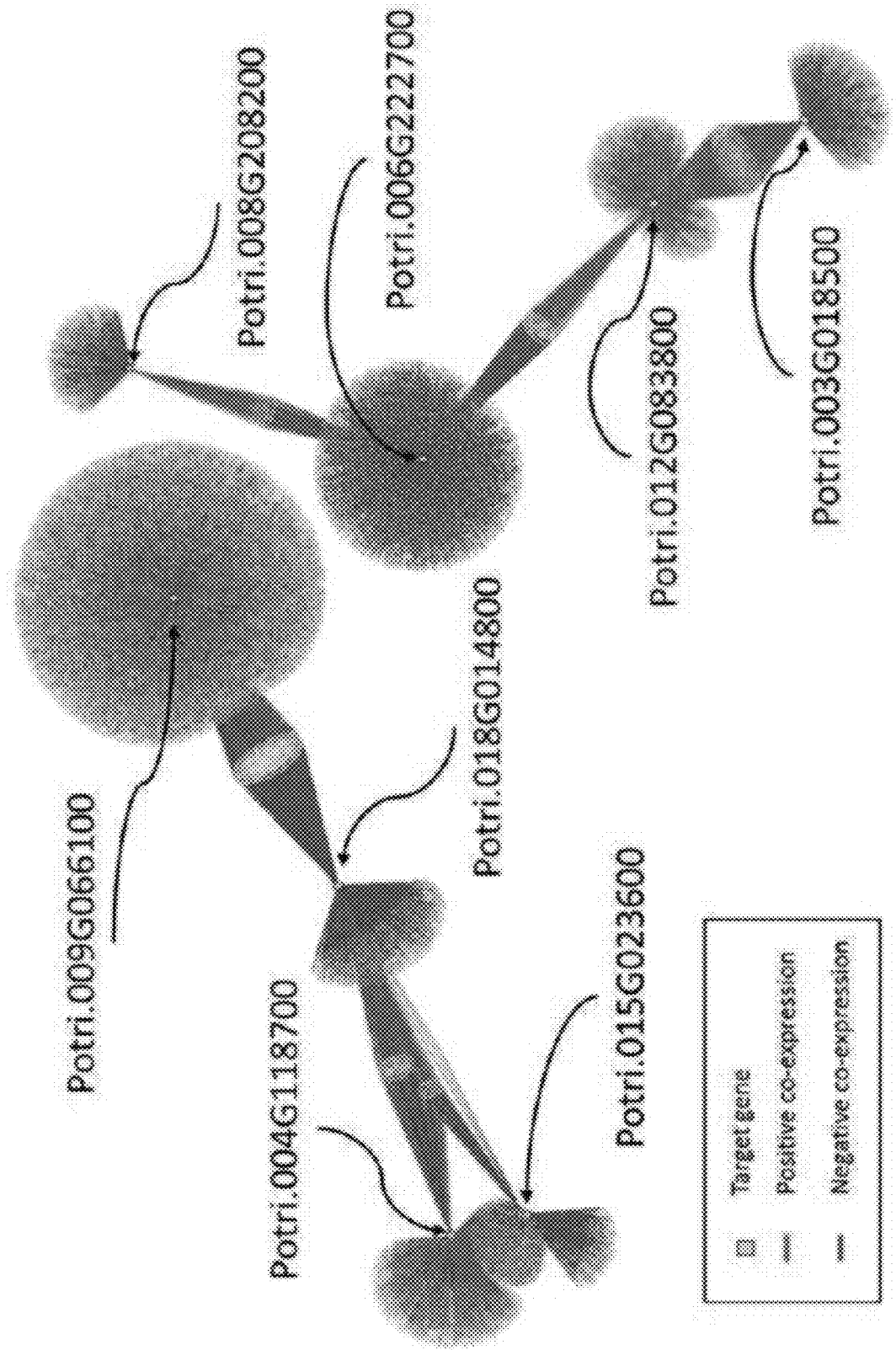
FIG. 3. Co-expression networks for the eight-significant genome-wide association loci related to callus formation and callus rating in *Populus*. Red edges indicate a positive co-expression at r≥0.9 and blue edges indicate negative coexpression at r≤−0.9.

Example 5: Callus Formation Genes Co-Expressed with Genes Related to Cell Differentiation and Growth Candidate genes from the GWAS were used as query in a co-expression of expressed genes in the Gene Atlas dataset (FIG. 3). The genome-wide co-expression network revealed that among the eight candidate genes, Potri.006G222700 and Potri.015G023600, were generally negatively co-expressed with their respective neighboring gene nodes in the co-expression network; while Potri.003G018500 (SOK1), Potri.012G083800, Potri.008G208200, Potri.009G066100 (MAPK3), and Potri.004G118700, were overwhelmingly positively co-expressed with their respective neighboring gene nodes in the co-expression network. Potri.015G023600 and Potri.004G118700 were the only two candidate genes that were co-expressed with each other. These two genes were also consistently and commonly negatively or positively co-expressed with 332 other genes, respectively, including 35 putative transcriptional regulators, 44 protein kinases, and 10 cell-cycle-related genes. Potri.006G222700 and Potri.012G083800 were also in a reciprocal co-expression network involving 77 genes including KNUCKLES (KNU) that mediates the repression of WUSCHEL (WUS), a floral meristem determinacy gene (homologous to AT5g14010), a phosphoribosyl transferase family protein involved in cellular biosynthesis (homologous to AT2g35390) and two genes related to microtubule organization. A group of genes which co-expressed simultaneously with three candidate genes (Potri.004G118700, Potri.015G023600 and Potri.018G014800 (CNDbr)) were identified. Generally, Potri.015G023600 was negatively co-expressed with this set of genes, while Potri.004G118700 and Potri.018G014800 (CNDbr) were positively co-expressed with this set of genes. This subnetwork involving co-expression with Potri.004G118700, Potri.015G023600 and Potri.018G014800 (CNDbr) includes genes related to arrested embryo development (Potri.010G020600, homologous to AT3g06350 (MEE32)) and a microtubule-binding protein (Potri.005G033200, homologous to AT3g05330 (TANGLED1)). In addition, the co-expressed gene neighborhoods for Potri.004G118700 and Potri.015G023600 were enriched for cell cycle and microtubule formation genes, whereas the neighborhood between Potri.006G222700 and Potri.008G208200 contained quite a few transcription factors and genes of unknown function. The distinctive positive and negative co-expression subnetworks (FIG. 3) strongly indicate tight orchestration of gene expression related to callus induction and repression.

Figure 4:
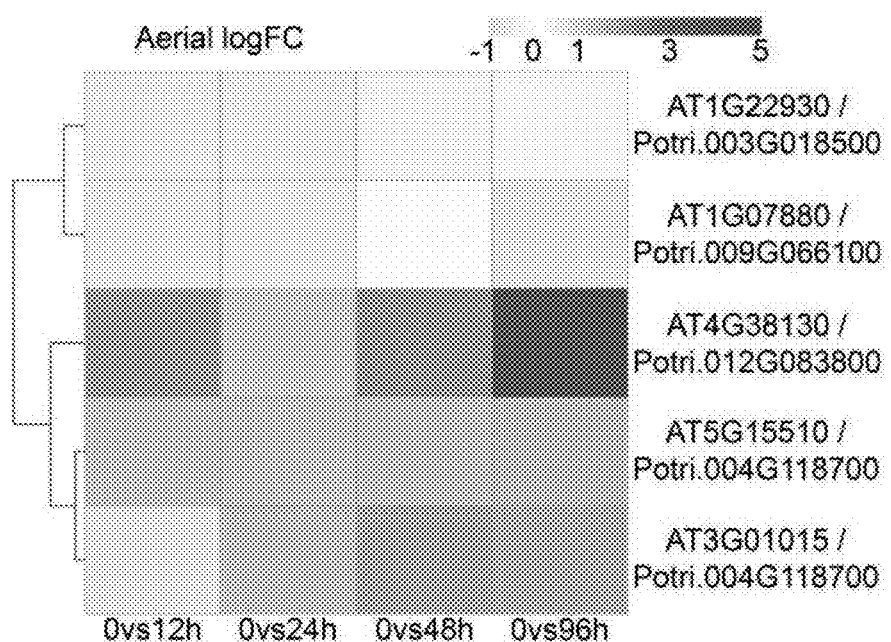
FIG. 4. Heat map of differentially expressed *Arabidopsis* orthologs, over 96 hours during callus induction, for *Populus* genes associated with callus formation or callus score in a genome-wide association study. Data taken from the NCBI GEO database.

Analysis of differential expression in *Arabidopsis thaliana* callus formation data from GEO (GSE29543) revealed that five orthologs to the candidate *Populus* genes were significantly differentially expressed in shoot callus formation in *Arabidopsis* (FIG. 4). Two of these orthologs (orthologous to Potri.004G118700 and Potri.012G083800) were upregulated during callus formation, while two alternate orthologs (Potri.009G066100 (MAPK3) and Potri.003G018500 (SOK1)) were downregulated during callus formation, again suggesting a network of genes that induce or repress callus formation.

Figure 5:
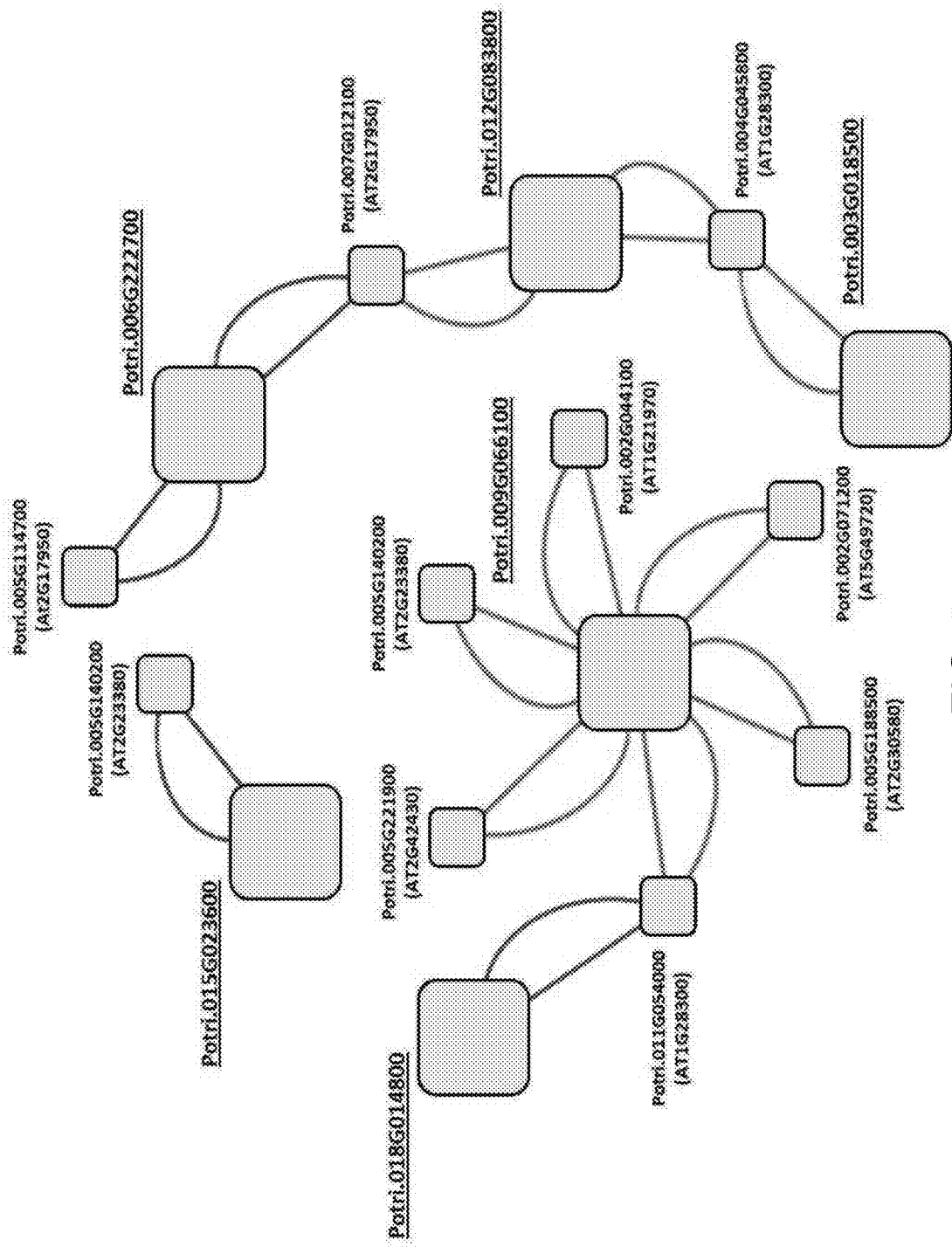
FIG. 5. Co-expression network for orthologs of *Arabidopsis* genes tested in transgenic experiments and their association with *Populus* callus formation and callus rating genes identified via genome-wide association approaches. *Arabidopsis* orthologs are presented in parenthesis and *Populus* candidate genes are underlined. The *Populus* genes were discovered using a GWAS approach; the *Arabidopsis* genes were significantly co-expressed with the candidate genes. Red edges indicate a positive co-expression at r>0.9 and blue edges indicate negative co-expression at r≤−0.9.

Interestingly, orthologs of genes reported in *Arabidopsis* transgenesis experiments do occur in the co-expression network. Two LBD16 genes, Potri.005G221900 (orthologous to AT2g42430) and Potri.002G041200 (orthologous to AT2g23380), are negatively co-expressed with Potri.009G066100 (MAPK3), along with Potri.002G044100 (orthologous to AT1g231970, LEC1, (Lotan T. et al., *Cell*. 1998; 93: 1195-205)), Potri.002G071200 (orthologous to AT5g49720, TSD1, (Frank M. et al., *The Plant J.* 2002; 29: 73-85)), Potri.005G188500 (orthologous to AT2g30580, BM1A, (Bratzel F. et al., *Curr Biol*. 2010; 20: 1853-9)), and Potri.011G054000 (orthologous to AT1g28300, LEC2, (Stone S L. et al., *Proc Natl Acad Sci USA*. 2001; 98: 11806-11)) (FIG. 5). Potri.011G054000 is also negatively co-expressed with the candidate gene Potri.018G014800 (CNDbr). A paralog of Potri.011G054000, Potri.004G045800 (LEC2) is positively co-expressed with both Potri.003G018500 (SOK1) and Potri.012G083800. Potri.007G012100 (orthologous to AT2g17950, WUS, (Zuo J. et al., *The Plant J.* 2002; 30: 349-59)) is positively co-expressed with Potri.012G083800 and negatively co-expressed with Potri.012G083800. Potri.005G140200 (orthologous to AT2g23380, CLF, (Chanvivattana Y. et al., *Development*. 2004; 131: 5263-76. PMID: 15456723)) was negatively co-expressed with Potri.015G023600.

Figure 6A:
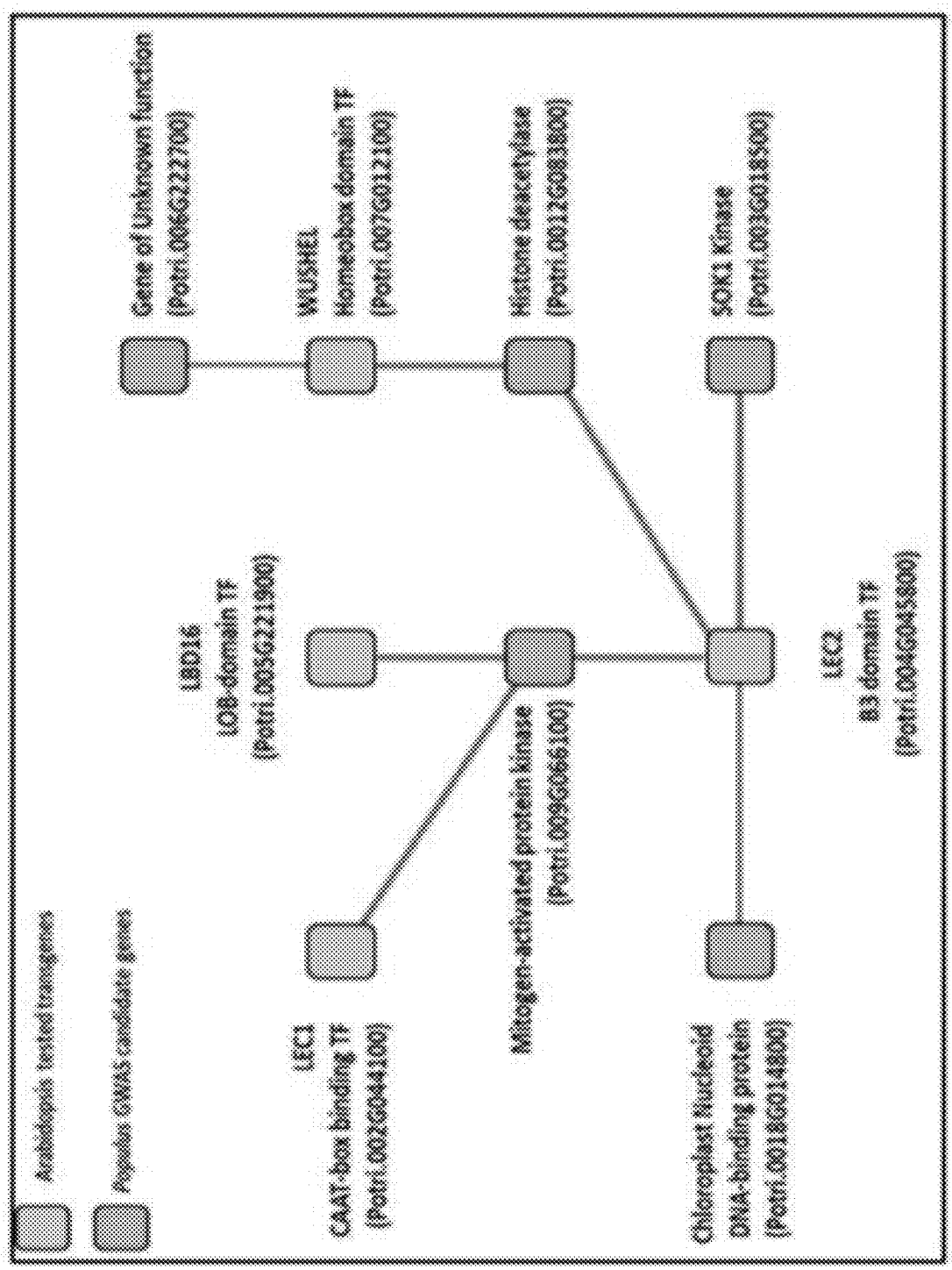
FIGS. 6A-6C. (A) Combined genome-wide association results and *Populus* co-expression analyses, with *Populus* homologs of *Arabidopsis*-tested transcription factors, in a proposed regulatory network. Gold boxes are *Populus* homologs of *Arabidopsis*-tested transcription factors; green boxes are GWAS identified *Populus* genes associated with callus formation. Red edges indicate positive co-expression, blue edges indicate negative co-expression. (B) The CNDbr, which negatively co-expressed with LEC2, was down-regulated in *Populus* leaf protoplasts when overexpressing LEC2. The other three genes (SOK1, MAPK3, and RPD3), positively co-expressed with LEC2, were not detected by qRT-PCR. Ctrl refers to the endogenous expression level of CNDbr in protoplasts while OE_LEC2 refers to the expression level of CNDbr when LEC2 was overexpressed in 3 independent replicates. The expression level of CNDbr was normalized to the ubiquitin internal control. (C) Expression patterns of five selected genes in co-expression network. LEC2 has extremely low abundance in leaves while CNDbr was highly expressed in leaves. SOK1, MAPK3, and RPD3 showed low abundances in leaf tissues.
Figure 6B:
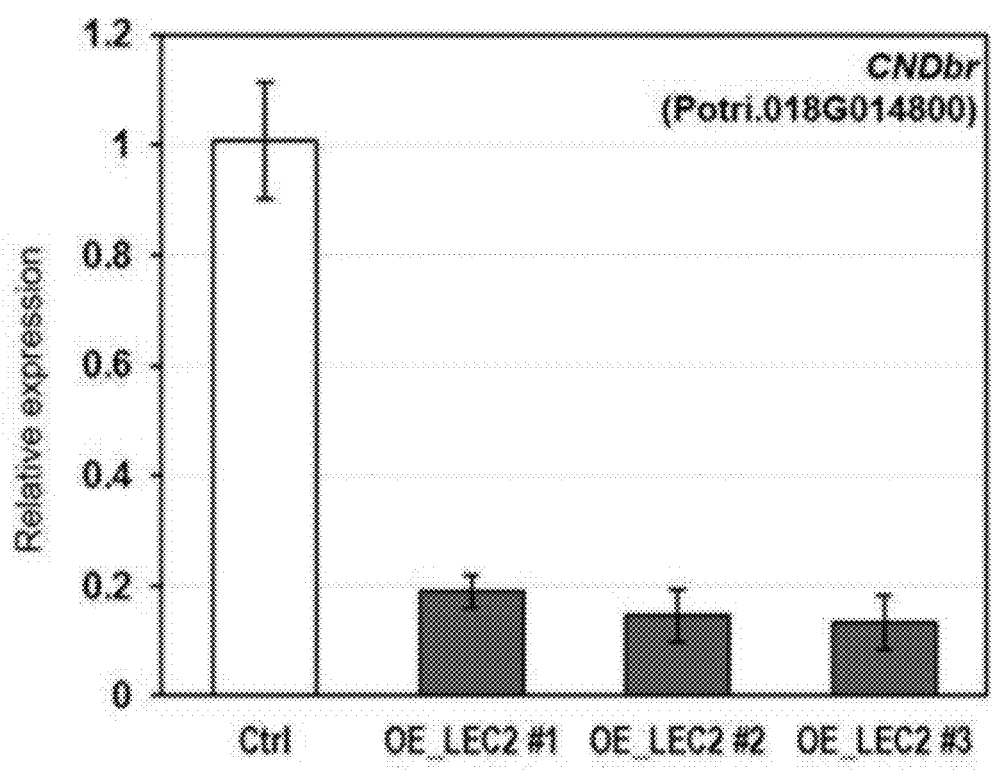
Figure 6C:
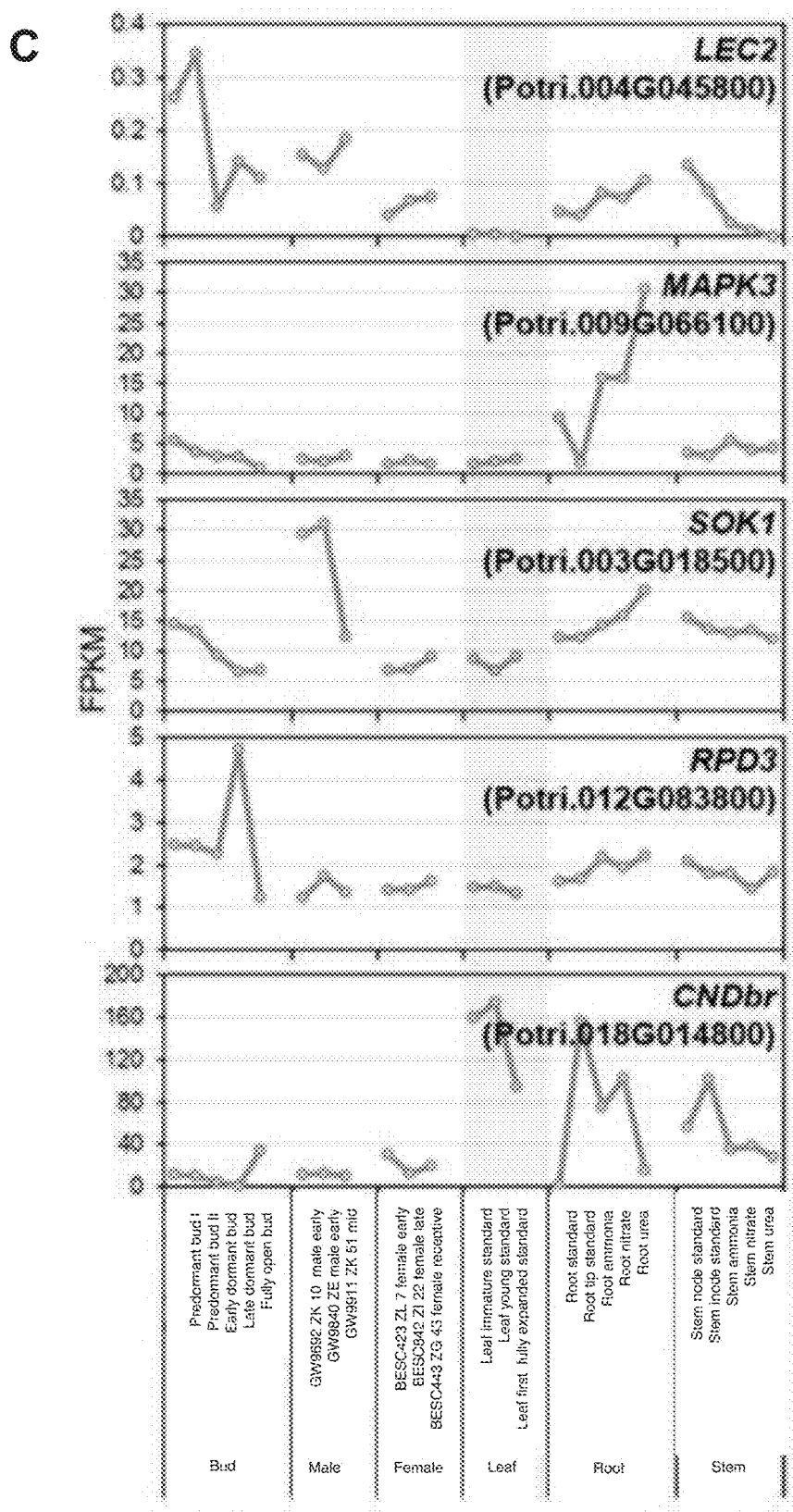

Co-expression of the candidate genes from this disclosure, with orthologs of genes functionally validated in callus formation in the model plant *Arabidopsis*, provides support for the GWAS approach used to identify genes targets involved in this process in *Populus*. Based on both GWAS results and the co-expression analyses of the *Populus* candidate genes with the tested and published *Arabidopsis* transgene results, the inventors propose a regulatory gene network for callus formation (FIG. 6A). Within this regulatory network, the gene encoding the transcription factor LEC2 containing the B3 domain showed either a positive or negative correlation to 4 of the 8 candidate GWAS genes identified in this study and may function as a hub gene control downstream expression of other transcription factors and kinases. Using a transient expression system in protoplast and quantitative RT-PCR (qRT-PCR), the inventors examined the ability of LEC2 to negatively regulate the expression of the Chloroplast Nucleoid DNA-binding-related gene (Potri.018G014800, CNDbr) and positively regulate the expression of SOK1, MAPK3 and RPD3 (Potri.003G018500 (SOK1), Potri.009G066100 (MAPK3) and Potri.012G083800, respectively). The inventors found that when LEC2 was constitutively overexpressed, CNDbr was significantly repressed (FIG. 6B); however, the three positively regulated candidate GWAS genes which also showed low abundance in leaf tissue, were not detected in the transient expression assay (FIG. 6C).

Example 6

Completely defining the genetic components of cell de-differentiation and callus formation is of broad interest and application. Induction of pluripotency has implications in understanding orchestrated cell proliferation as well as normal tissue and organ development. Here, the inventors identified eight genes associated with callus formation or callus rating in *Populus*. These eight loci were distributed across the *Populus* genome on chromosomes III, IV, XI, VIII, IX, XII, XV and XVII. All eight loci have paralogs within the *Populus* genome that were the result of the Salicoid duplication event that occurred approximately 64 mya (Tuskan G A. et al., *Science*. 2006; 313: 1596-604). None of the paralogs showed significant association with callus formation or callus rating, suggesting that subfunctionalization may have occurred in these gene lineages. Among the eight significant associations, Potri.004G118700, Potri.008G082100 and Potri.009G066100 (MAPK3) are co-expressed with genes annotated with functions related to cell division and cell differentiation; Potri.012G083800 is known to affect chromatin remodeling and an ortholog of Potri.008G208200 has been reported to be potentially involved in callus formation in sugarcane (Mingossi F B. et al., *Plant Mol Biol*. 2010; 73: 271-81). In total, the evidence suggests that there are networks of genes that tightly regulate the cell division and cell differentiation cascade controlling callus formation.

Potri.004G118700, LEC2, may function as upstream regulator of several genes related to callus formation, including Potri.003G018500 (SOK1), Potri.009G066100 (MAPK3), Potri.012G083800 and Potri.018G014800 (CNDbr) (FIG. 6A). Specifically, Potri.003G018500 (SOK1), a SUPPRESSOR OF KINASE (SOK1) kinase, belongs to the STE20/SPS1/GC kinase family (Pfam PF05794), and there are multiple frameshift mutants at this locus within the GWAS population that cause a gained stop codon at position Chr03:2242626 bp. STE20 kinases in general are thought to regulate MAPK cascades, including several eukaryotic T-complex protein 11 (Tcp11)-related sequences. In yeast, a SOK1 protein, sharing sequence homology to a testis-specific mouse gene, suppresses cyclic AMP-dependent protein kinase mutants. Deletions in SOK1 in *Saccharomyces* can lead to an increase in lifespan of 15% or higher (Managbanag J. et al., *PloS One*. 2008; 3: e3802). The human homolog to mouse Tcp11 is only expressed in fertile adult testes and is thought to be important in sperm function and fertility (Ma Y. et al., *Mol Human Reprod*. 2002; 8: 24-31). The SOK1 or MST4 family of kinases are known signaling molecules for cell proliferation in multicellular organisms and have been implicated in cancer (Thompson B J. et al., *J Cell Biol*. 2015; 210: 871-82).

Potri.009G066100 (MPK3), a member of a 21-gene family comprised of four groups and is orthologous to the defense-related gene AtMPK3 (Nicole M-C. et al., BMC Genomics. 2006; 7: 223). MPKs are generally involved in directing cellular responses to a variety of stimuli, such as osmotic stress and heat shock, and they regulate cell functions, including proliferation, gene expression, differentiation, mitosis, cell survival, and apoptosis (Pearson G. et al., *Endocr Rev*. 2001; 22: 153-83). Interestingly, homologs of PtMPK3 in humans have been linked to various forms of cancer Chano T. et al., *Nat Genet.* 2002; 31: 285-9.

Potri.012G083800, a RPD3 HISTONE DEACETYLASE (RDP3), is present as a single copy gene in *Populus* and is found as co-orthologs in all sequenced plant genomes. Potri.012G083800 shares sequence similarity with two *Arabidopsis* RNA-MEDIATED TRANSCRIPTIONAL SILENCING 1 genes (At5g63110 and At5g35600). Histone acetylation/deacetylation, in combination with various MAPKs, has been reported to play a role in plant defense (Hollender C. et al., *J Integr Plant Biol.* 2008; 50: 875-85). Histone deacetylases are primarily involved in regulating DNA transcription via modification of histone and chromatin structure and are often implicated in cellular processes such as cell growth, cell cycle and apoptosis. Posttranslational modification of histones has an intriguing but not fully understood role in human cancer (Cohen I. et al., *Genes & Cancer.* 2011; 2: 631-47). Moreover, histone acetylase PRZ1 in *Arabidopsis* acts as a transcriptional coactivator to modulate auxin effects on gene expression. Whereas auxin promotes formation of lateral roots in wild type, and both auxin and cytokinin are necessary for callus formation, prz1-1 mutants will produce callus in the presence of either auxin or cytokinin (Sieberer T. et al., *Curr Biol.* 2003; 13: 837-42; Anzola J M. et al., *Proc Natl Acad Sci USA.* 2010; 107: 10308-13). In humans, histone acetylation/deacetylation has been linked to chronic myeloid leukemia. Histone deacetylase has also been reported to impact open chromatin and increase gene expression in pluripotent human cancer cells (Gaspar-Maia A. et al., *Nat. Rev. Mol. Cell Biol.* 2011; 12: 36). Potri.012G083800 appears to be a candidate gene for midstream control of signal transduction of cell proliferation in *Populus*.

Potri.018G014800 is a CHLOROPLAST NUCLEOID DNA-BINDING-RELATED (CNDbr)/Aspartyl protease (Pfam00026) and variants within the GWAS contain a premature stop codon at position Chr18:1196058 bp that is associated with higher callus formation. In tobacco, CNDbr proteins have proteolytic activity and have been shown to bind to DNA (Diaz-Mendoza M. et al., *Genet Mol Biol.* 2016; 39: 329-38). CNDbr proteins have also been linked to leaf senescence (Kato Y. et al., *Planta.* 2005; 222: 643-51). In humans, proteins containing aspartyl protease domains includes the gene encoding Cathepsin D (CTSD), which has been implicated in breast cancer, and the gene encoding Cathepsin E (CTSE), which has been implicated in stomach cancer (Olson O C. et al., *Nat. Rev. Cancer.* 2015; 15: 712-29). Although annotated as a CHLOROPLAST NUCLEOID DNA-BINDING-RELATED protein, Potri.018G014800 (CNDbr) may primarily be related to general cell differentiation.

Several transcription factors, including LEC2, have been implicated in ectopic callus formation in *Arabidopsis* through transgenic studies. Ikeda and Ohme-Takagi (2014) have implicated WIND1, WUS and TCP as genes that regulate callus formation (Ikeda M. et al., *Front Plant Sci.* 2014; 5). LATERAL ORGAN BOUNDARIES DOMAIN (LBD16) transcription factors have also been reported to induce callus formation in *Arabidopsis* (Fan M. et al., *Cell Res.* 2012; 22: 1169). And, ectopic overexpression of OPB4, another transcription factor, resulted in enhanced callus formation in *Arabidopsis* (Ramirez-Parra E. et al., *New Phytol.* 2017; 213: 1787-801). And, Iwase et al. (2013) successfully overexpressed AtWND1 to promote callus formation in phytohormone-free medium in tobacco (Iwase A. et al., *Plant Signal Behav.* 2013; 8: e27432). Surprisingly, none of the orthologs to the transcription factors described above showed significant associations with callus formation in *Populus* in the GWAS analysis. This difference could be related to species-specific differences in regulating and inducing callus, however it is more likely that these differences are due to experimental approach. The GWAS approach was conducted with no a priori assumptions concerning which genes were controlling callus formation, and thus identified only those loci that satisfied the statistical thresholds. The GWAS-identified genes, particularly, SOK1 and MAPK3, may be acting as checkpoints that monitor environmental queues, as discussed above. Such checkpoint genes could be overwhelmed by ectopic regulator expression in *Arabidopsis*. Human cell checkpoint genes are known to sense environmental signals such as ribonucleotide pools or oxygen tension and can lead to tumor formation if mutated (McDonald E R. et al., Ann Med. 2001; 33(2):113-22. PMID: 11327114). It may also be that the orthologs of those genes tested in *Arabidopsis* did not vary in the population and therefore were not detectable using GWAS approaches.

However, there is substantial SNP variation across *Populus* orthologs of these *Arabidopsis* genes. It is also possible that the *Arabidopsis* orthologs are indeed influencing callus formation in *Populus*, but to a lesser degree than the genes identified in the GWAS test. Ectopic overexpression approaches may overwhelm innate gene and gene network influences on callus formation and impair de novo gene discovery. Ectopic overexpression of transcription factors likely leads to perturbations in multiple downstream phenotypes.

In support of de novo gene discovery via GWAS approaches, the Affymetrix resource developed for callus induction in *Arabidopsis* was examined and significant fold change was found in four orthologs of the eight candidate genes. Interestingly, the two kinases discovered, Potri.003G018500 (SOK1) and Potri.009G066100 (MAPK3), display significant negative fold change after 96 hours, while a gene with strong homology to human malignancy, Potri.008G208200, displayed a significant 4-fold change in expression after 96 hours. In further support of de novo discovery approaches, the eight genes reported here are significantly co-expressed with genes related to cytokinesis, tubulin, spindle function, and cell differentiation.

What is claimed is:

1. A genetically modified *Populus* plant, plant cell or plant tissue, wherein the expression of an endogenous suppressor of kinase 1 (SOK1) gene is altered in the *Populus* plant, plant cell or plant tissue, wherein the alteration comprises inactivation of the endogenous SOK1 gene in the *Populus* plant, plant cell or plant tissue, resulting in increased callus formation by the *Populus* plant cell, or increased callus formation in the *Populus* plant or plant tissue, and wherein the endogenous SOK1 gene encodes an enzyme with at least 98% sequence identity to SEQ ID NO: 23.

2. The genetically modified *Populus* plant, plant cell or plant tissue of claim 1, wherein the inactivation of the endogenous SOK1 gene is achieved by introducing a nucleic acid inhibitor of the selected gene to the *Populus* plant, plant cell or plant tissue.

3. The genetically modified *Populus* plant, plant cell or plant tissue of claim 2, wherein the nucleic acid inhibitor is selected from the group consisting of an antisense RNA, a small interfering RNA, an RNAi, a microRNA, an artificial microRNA, and a ribozyme.

4. The genetically modified *Populus* plant, plant cell or plant tissue of claim 1, wherein the inactivation of the endogenous SOK1 gene is achieved by genome editing, which is achieved by a method selected from the group consisting of CRISPR/Cas system, Cre/Lox system, TALEN system, ZFNs system and homologous recombination.

5. The genetically modified *Populus* plant, plant cell or plant tissue of claim 4, wherein the CRISPR-mediated genome editing comprises introducing into the *Populus* plant a first nucleic acid encoding a Cas9 nuclease, a second nucleic acid comprising a guide RNA (gRNA), wherein said gRNA is specific to the endogenous SOK1 gene.

6. A method for increasing callus formation, comprising altering in a *Populus* plant, plant cell or plant tissue the expression of a SOK1 gene or a homolog thereof, wherein the alteration comprises inactivation of the endogenous SOK1 gene in the *Populus* plant, plant cell or plant tissue, resulting in increased callus formation by the *Populus* plant cell, or increased callus formation in the *Populus* plant or plant tissue, and wherein the endogenous SOK1 gene encodes an enzyme with at least 98% sequence identity to SEQ ID NO: 23.

7. The method of claim 6, wherein the inactivation of the endogenous SOK1 gene is achieved by introducing a nucleic acid inhibitor of the selected gene to the *Populus* plant, plant cell or plant tissue.

8. The method of claim 7, wherein the nucleic acid inhibitor is selected from the group consisting of an antisense RNA, a small interfering RNA, an RNAi, a microRNA, an artificial microRNA, and a ribozyme.

9. The method of claim 6, wherein the inactivation of the endogenous SOK1 gene is achieved by genome editing, which is achieved by a method selected from the group consisting of CRISPR/Cas system, Cre/Lox system, TALEN system, ZFNs system and homologous recombination.

10. The method of claim 9, wherein the CRISPR-mediated genome editing comprises introducing into the *Populus* plant a first nucleic acid encoding a Cas9 nuclease, a second nucleic acid comprising a guide RNA (gRNA), wherein said gRNA is specific to the endogenous SOK1.

11. The genetically modified *Populus* plant, plant cell or plant tissue of claim 1, wherein said *Populus* is *Populus trichocarpa*.

12. The method of claim 6, wherein said *Populus* is *Populus trichocarpa*.

* * * * *